United States Patent
Tsai et al.

(10) Patent No.: US 10,760,110 B2
(45) Date of Patent: Sep. 1, 2020

(54) ANTIBIOTIC TESTING AND SCREENING SYSTEM

(71) Applicant: KeMyth Biotech Co., Ltd., Taipei (TW)

(72) Inventors: Yu-Kuo Tsai, Taipei (TW); Leung-Kei Siu, Taipei (TW)

(73) Assignee: KeMyth Biotech Co., Ltd., Taipei (TW)

(*) Notice: Subject to any disclaimer, the term of this patent is extended or adjusted under 35 U.S.C. 154(b) by 0 days.

(21) Appl. No.: 15/903,843

(22) Filed: Feb. 23, 2018

(65) Prior Publication Data

US 2018/0245125 A1  Aug. 30, 2018

Related U.S. Application Data

(60) Provisional application No. 62/463,168, filed on Feb. 24, 2017.

(51) Int. Cl.

| | | |
|---|---|---|
| *G01N 33/53* | (2006.01) | |
| *C12Q 1/18* | (2006.01) | |
| *C12Q 1/06* | (2006.01) | |
| *C12N 1/20* | (2006.01) | |
| *C12Q 1/6827* | (2018.01) | |
| *C12Q 1/24* | (2006.01) | |
| *C12N 15/10* | (2006.01) | |
| *C12Q 1/02* | (2006.01) | |
| *G01N 33/94* | (2006.01) | |

(52) U.S. Cl.
CPC ........... *C12Q 1/18* (2013.01); *C12N 1/20* (2013.01); *C12N 15/1079* (2013.01); *C12Q 1/025* (2013.01); *C12Q 1/06* (2013.01); *C12Q 1/24* (2013.01); *C12Q 1/6827* (2013.01); *G01N 33/9446* (2013.01)

(58) Field of Classification Search
None
See application file for complete search history.

(56) References Cited

FOREIGN PATENT DOCUMENTS

| WO | WO 2003012130 | * | 2/2013 |
| WO | WO 201602927 | * | 6/2016 |

OTHER PUBLICATIONS

Mimoz et al (Antimicrob Agents Chemother 2012; 56: 2759-60).*
Tadesse et al (Microbial Drug Resistance (Sep. 1, 2018) vol. 24, No. 7, pp. 939-948,).*

* cited by examiner

*Primary Examiner* — Jennifer E Graser
(74) *Attorney, Agent, or Firm* — Wolf, Greenfield & Sacks, P.C.

(57) ABSTRACT

The present invention provides a platform technology for testing, screening, selecting and evaluating antibiotics by using genetically engineered strains with identified, individual or combined, resistance mechanisms, prepared from fully susceptible clinical isolates. This antibiotic testing and screening system of the present invention can efficiently and effectively evaluate antibiotics against specified resistance mechanisms in vitro and in vivo, and is suitable on the novel antibiotic development in against multidrug-resistant bacteria.

6 Claims, 1 Drawing Sheet
Specification includes a Sequence Listing.

ANTIBIOTIC TESTING AND SCREENING SYSTEM

RELATED APPLICATION

This application claims priority to U.S. Provisional Application No. 62/463,168, filed on Feb. 24, 2017, the content of which is hereby incorporated by reference in its entirety.

FIELD OF THE INVENTION

The present invention relates to a platform technology for evaluating the antimicrobial activity of a known antibiotic against specified resistance mechanisms and also for screening for new antimicrobial agents.

BACKGROUND OF THE INVENTION

The emergence of antibiotic resistance has become a major clinical and public health threat worldwide.[1,2] According to a recent report from the United Kingdom, if antimicrobial resistance continues to increase, 10 million people will die due to it annually by 2050, a mortality rate greater than that of cancer.[1] Correct use of antibiotics and the development of novel antibiotics are both necessary to overcome this crisis.

World Health Organization (WHO) reported an extremely high resistant rates in *Klebsiella pneumoniae, Escherichia coli* and *Staphylococcus aureus*, which are common causes of hospital and community infections.[4] *K. pneumoniae* and *E. coli* both belong to Enterobacteriaceae and have similar antibiotic resistance mechanisms.[5] Understanding the antibiotic effectiveness against each resistant mechanism can help us to develop and use antibiotics. Traditionally, a large number of clinical drug-resistance isolates are collected and used for testing and screening antibiotics before going into clinical trials.[6] However, the resistance mechanisms in clinical isolates usually are complex and not fully identified. It is difficult to verify which mechanism is actually involved or plays the major role in conferring the drug resistance. Without the certain information, it is also difficult to modify the antibiotic candidates for improving its antimicrobial activity in an efficient manner.

SUMMARY OF THE INVENTION

The present design provides a platform technology for testing, screening, selecting and evaluating antibiotics by using genetically engineered strains with identified, individual or combined, resistance mechanisms, prepared from a multidrug (or preferably fully) susceptible clinical isolate.

Specifically, the present invention provides a platform technology for screening for antimicrobial agents by using genetic engineering bacterial strains, wherein these bacterial strains before genetic engineering are in nature highly susceptible to antibiotic treatment (preferably susceptible to multiple antibiotic treatment) and after genetic engineering it is given one or more mutations or antibiotic resistance genes based on the major types of drug-resistant mechanisms, selected form the group consisting of (i) decrease antibiotic permeability by loss of outer membrane proteins, (ii) pump out the antibiotics by overexpression of efflux pumps, (iii) eliminates or reduces binding of antibiotic by modification of antibiotic target or by acquirement of antibiotic-resistant target, and (iv) inactivate antibiotic by enzymatic cleavage or modification, and any combinations thereof. Since the drug-resistant mechanism given in the genetic engineering bacterial strains is known and identified, once an agent is cultured with the genetic engineering bacterial strain and determined to have an antimicrobial activity against it, we can thus figure out that the agent is specifically active against the drug-resistant mechanism given in the genetic engineering bacterial strains. Accordingly, the platform technology of the invention is feasible and efficient to identify an antimicrobial agent targeting a particular drug-resistant mechanism as desired. In addition, the platform technology of the invention, as compared with a conventional screening method using clinical resistant isolates, is less labor intensive and also is workable for carrying out a large-scale screening for an antimicrobial agent, especially for an antimicrobial agent active against multiple drug-resistant mechanisms, and moreover is meaningful to apply the selected antimicrobial agent to subsequent drug modification.

In particular, the present invention provides a method for screening for an antimicrobial agent, comprising:

(1) providing a wild-type (WT) susceptible bacterial strain which has a WT-referenced resistance level to a reference antibiotic;

(2) providing a first genetic engineering bacterial strain generated from the WT susceptible bacterial strain which is given a first mutation or antibiotic resistance gene (ET1) via a genetic engineering manner to confer drug resistance to the reference antibiotic, exhibiting a ET1-referenced resistance level to the reference antibiotic, wherein the ET1-referenced resistance level is higher than the WT-referenced resistance level;

(3) culturing the wild-type susceptible bacterial strain in the presence of a first test agent and analyzing the first test agent for its activity against the wild-type susceptible bacterial strain to obtain a WT-Test1 resistance level;

(4) culturing the first engineered bacterial strain in the presence of the first test agent and analyzing the first test agent for its activity against the first engineered bacterial strain to obtain a ET1-Test1 resistance level;

(5) obtaining a ET1-Test1 ratio of the ET1-Test1 resistance level to the WT-Test1 resistance level; and (6) determining if the first test agent is a potentially effective antimicrobial agent against the drug resistance associated with ET1 in the first engineered bacterial strain based on the ET1-Test1 ratio.

In some embodiments, the ET1-referenced resistance level is higher than the WT-referenced resistance level by 1-fold, 2-fold, 3-fold, or 4-fold or more.

In some embodiments, the wild-type susceptible bacterial strain is susceptible to multiple antibiotics, selected from the group consisting of β-lactams, quinolones, aminoglycosides, tetracyclines, folate pathway inhibitors, polymyxins, phenicols, fosomycins, nitrofurans and any combinations thereof.

In some embodiments, the first test agent is determined as a potentially effective antimicrobial agent against the drug resistance associated with ET1 if the ET1-Test1 ratio is no more than 4 (e.g. 4 or less, 3 or less, 2 or less, 1 or less).

In more particular, the method of the invention further comprises:

(7) (17) culturing the wild-type susceptible strain in the presence of a second test agent and analyzing the second test agent for its activity against the wild-type susceptible strain to obtain a WT-Test2 resistance level;

(8) (18) culturing the first engineered bacterial strain in the presence of the second test agent and analyzing the second test agent for its activity against the first engineered bacterial strain to obtain a ET1-Test2 resistance level;

(9) (19) obtaining a ET1-Test2 ratio of the ET1-Test2 resistance level to the WT-Test2 resistance level; and

(10) (20) determining if the second test agent is a potentially effective antimicrobial agent against the drug resistance associated with ET1 in the first engineered bacterial strain based on the ET1-Test2 ratio.

In some embodiments, the second test agent is determined as a potentially effective antimicrobial agent against the drug resistance associated with ET1 if the ET1-Test2 ratio is no more than 4 (e.g. 4 or less, 3 or less, 2 or less, 1 or less).

In some embodiments, the second test agent is determined as a potentially effective antimicrobial agent against the drug resistance associated with ET1 if the ET1-Test2 resistance level, which is expressed by minimum inhibitory concentration (MIC), is no more than 10 μg/ml, 5 μg/ml, 2.5 μg/ml, 1 μg/ml or 0.5 μg/ml.

In more particular, the method of the invention further comprises:

(11) ranking the first test agent and the second test agent for a preferable antimicrobial activity according to the ET1-Test1 ratio and the ET1-Test2 ratio, the lower the ratio, the higher the ranking.

In more particular, the method of the invention further comprises:

(12) providing a second engineered bacterial strain generated from the WT susceptible bacterial strain which is given a second mutation or antibiotic resistance gene (ET2) in a genetic engineering manner to confer drug resistance to the reference antibiotic, exhibiting a ET2-referenced resistance level to the reference antibiotic, wherein the ET2-referenced resistance level is higher than the WT-referenced resistance level;

(13) culturing the second engineered bacterial strain in the presence of the first test agent and analyzing the first test agent for its activity against the second engineered bacterial strain to obtain a ET2-Test1 resistance level;

(14) obtaining a ET2-Test1 ratio of the ET2-Test1 resistance level to the WT-Test1 resistance level;

(15) determining if the first test agent is a potentially effective antimicrobial agent against the drug resistance associated with ET2 in the second engineered bacterial strain based on the ET2-Test1 ratio.

In some embodiments, the first test agent is determined as a potentially effective antimicrobial agent against the drug resistance associated with ET2 if the ET2-Test1 ratio is no more than 4 (e.g. 4 or less, 3 or less, 2 or less, 1 or less).

In some embodiments, the first test agent is determined as a potentially effective antimicrobial agent against the drug resistance associated with ET2 if the ET2-Test1 resistance level, which is expressed by minimum inhibitory concentration (MIC), is no more than 10 μg/ml, 5 μg/ml, 2.5 μg/ml, 1 μg/ml or 0.5 μg/ml.

In more particular, the method of the invention further comprises: (16) obtaining a first sum ratio value with respect to the first test agent by adding the ET1-Test1 ratio to the ET2-Test1 ratio.

In more particular, the method of the invention further comprises:

(17) culturing the wild-type susceptible strain in the presence of a second test agent and analyzing the second test agent for its activity against the wild-type susceptible strain to obtain a WT-Test2 resistance level;

(18) culturing the first genetic engineering bacterial strain in the presence of the second test agent and analyzing the second test agent for its activity against the first genetic engineering bacterial strain to obtain a ET1-Test2 resistance level;

(19) obtaining a ET1-Test2 ratio of the ET1-Test2 resistance level to the WT-Test2 resistance level; and

(20) determining if the second test agent is a potentially effective antimicrobial agent against the drug resistance associated with ET1 in the first genetic engineering bacterial strain based on the ET1-Test2 ratio.

In some embodiments, the second test agent is determined as a potentially effective antimicrobial agent against the drug resistance associated with ET1 if the ET1-Test2 ratio is no more than 4 (e.g. 4 or less, 3 or less, 2 or less, 1 or less).

In some embodiments, the second test agent is determined as a potentially effective antimicrobial agent against the drug resistance associated with ET1 if the ET1-Test2 resistance level, which is expressed by minimum inhibitory concentration (MIC), is no more than 10 μg/ml, 5 μg/ml, 2.5 μg/ml, 1 μg/ml or 0.5 μg/ml.

In more particular, the method of the invention further comprises:

(21) culturing the second engineered bacterial strain in the presence of the second test agent and analyzing the second test agent for its activity against the second engineered bacterial strain to obtain a ET2-Test2 resistance level;

(22) obtaining a ET2-Test2 ratio of the ET2-Test2 resistance level to the WT-Test2 resistance level;

(23) determining if the second test agent is a potentially effective antimicrobial agent against the drug resistance associated with ET2 in the second engineered bacterial strain based on the ET2-Test2 ratio.

In some embodiments, the second test agent is determined as a potentially effective antimicrobial agent against the drug resistance associated with ET2 if the ET2-Test2 ratio is no more than 4 (e.g. 4 or less, 3 or less, 2 or less, 1 or less).

In some embodiments, the second test agent is determined as a potentially effective antimicrobial agent against the drug resistance associated with ET2 if the ET2-Test2 resistance level, which is expressed by minimum inhibitory concentration (MIC), is no more than 10 μg/ml, 5 μg/ml, 2.5 μg/ml, 1 μg/ml or 0.5 μg/ml.

In more particular, the method of the invention further comprises: (24) obtaining a second sum ratio value with respect to the second test agent by adding the ET1-Test2 ratio to the ET2-Test2 ratio.

In more particular, the method of the invention further comprises: (25) ranking the first test agent and the second test agent for a preferable antimicrobial activity according to the first sum ratio value and the second sum ratio value, the lower the value, the higher the ranking.

In more particular, the method of the invention further comprises: (26) ranking the first test agent and the second test agent for a preferable antimicrobial activity according to the ET2-Test1 ratio and the ET2-Test2 ratio, the lower the ratio, the higher the ranking.

In some embodiments, the preferable antimicrobial activity includes an antimicrobial activity against multiple drug-resistance mechanisms.

In some embodiments, the first mutation or antibiotic resistance gene, or the second mutation or antibiotic resistance gene is given based on one or more drug-resistant mechanisms selected form the group consisting of (i) decrease antibiotic permeability by loss of outer membrane proteins, (ii) pump out the antibiotics by overexpression of efflux pumps, (iii) eliminates or reduces binding of antibiotic by modification of antibiotic target or by acquirement of antibiotic-resistant target, and (iv) inactivate antibiotic by enzymatic cleavage or modification, and any combinations thereof.

In some embodiments, the first mutation or antibiotic resistance gene, or the second mutation or antibiotic resistance gene is selected from the group consisting of: ΔompK35, ΔompK36, ΔramR, GyrA S83I, GyrA S83L, GyrA S83F, GyrA S83Y, GyrA D87N, ParC S80I, CTX-M-14, CTX-M-15, SHV-12, CMY-2, DHA-1-AmpR, KPC-2, KPC-3, IMP-8, NDM-1, VIM-1, OXA-48, QnrB, QnrS, AAC(6')-Ib-cr, AAC(6')-Ib-cr, AAC(3)-IId, AAC(3)-IVa, ANT(2")-Ia, ANT(3")-Ia, APH(3')-Ia, APH(3')-IIa, StrA-StrB, ArmA, RmtB, Tet(A), Tet(B), Tet(C), Tet(D), Tet(M), Sul1, Sul2, DfrA1, DfrA16, AdeR D20N, AdeR A91V, AdeR P116L, AdeS G30D, AdeS A94V, AdeS R152K, AdeS T153M, ParC G78C, ParC S80L, ParC S80W, ParC S80Y, ParC E84K, VEB-3, ADC-30, IMP-1, OXA-23, OXA-58, OXA-66, OXA-72, AAC(3)-IIa, APH(3')-VIa, and any combinations thereof.

In some embodiments, the first mutation or antibiotic resistance gene, or the second mutation or antibiotic resistance gene is given by a chromosome-mediated approach or a plasmid-mediated approach.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1A:
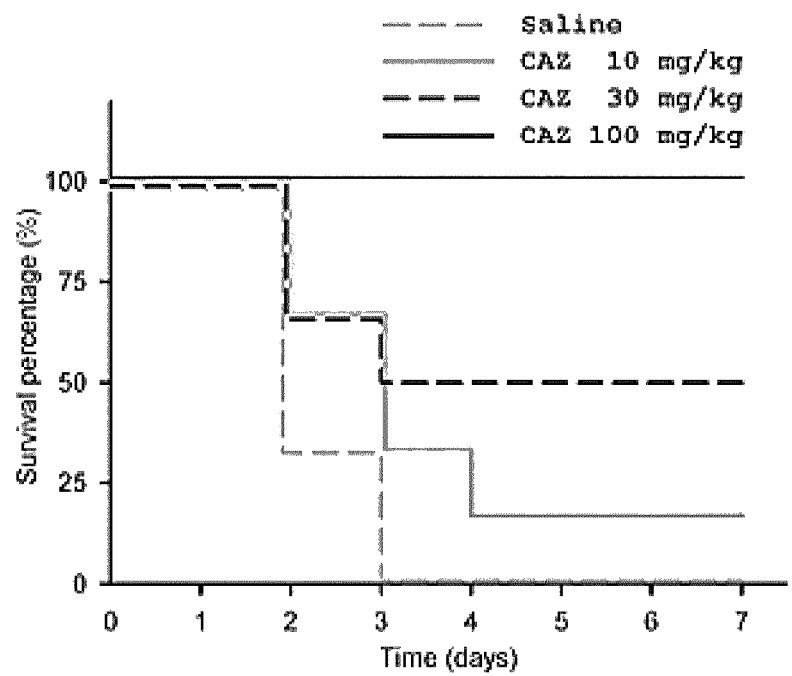
FIGS. 1A and 1B show in vivo efficacy of ceftazidime (FIG. 1A) and cefotaxime (FIG. 1B) against *K. pneumoniae* NVT1001 harboring the pACYC177 plasmid with $bla_{OXA-48}$ in a mouse peritonitis-sepsis model.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "drug resistance" can refer to a cell's increasing resistance to drug treatment, such as antibiotic treatment.

As used herein, the terms "susceptible" and "antibiotic susceptibility" can indicate that the growth of a microorganism is inhibited by a normal achievable concentration of an antimicrobial agent when the recommended dosage is used.

As used herein, the terms "resistant" and "antibiotic resistance" can indicate that microorganism growth is not inhibited by a normal achievable concentration of the agent and clinical efficacy of the agent against the microorganism has not been shown in treatment studies.

As used herein, a resistance level with reference to a bacterial strain for a particular agent can indicate a minimal amount of the particular agent that will inhibit the visible growth of a microorganism, such as a minimum inhibitory concentration (MIC). A bacterial strain with a lower resistance level to an agent can indicate that the bacterial strain is relatively susceptible to the agent (reflecting a relatively lower MIC), while a bacterial strain with a higher resistance level to an agent can indicate that the bacterial strain is relatively resistant to the agent (reflecting a relatively higher MIC).

According to the present invention, a bacterial strain can be from any bacterial species, particularly a species leading to common infectious diseases in human, including but not limited to, Gram-negative bacteria, such as *K. pneumonia*, *Escherichia coli*, *Salmonella* spp., *Acinetobacter baumannii* and *Pseudomonas aeruginosa*, and Gram-positive bacteria, such as *Staphylococcus aureus* and *Enterococcus* spp.

As used herein, a wild-type susceptible bacterial strain can indicate a bacterial strain, the genome of which is not modified by a genetic engineering manner and which is susceptible to antibiotic treatment. Preferably, a wild-type susceptible bacterial strain as used herein is susceptible to multiple antibiotics, selected from the group consisting of β-lactams, quinolones, aminoglycosides, tetracyclines, folate pathway inhibitors, polymyxins, phenicols, fosomycins, nitrofurans and any combinations thereof. A particular example of a wild-type susceptible bacterial strain as used herein includes *K. pneumoniae* strain NVT1001, which can be obtained for example from Division of Infectious Diseases and Tropical Medicine, Department of Internal Medicine, Tri-Service General Hospital, Taipei 114, Taiwan.

As used herein, a genetically engineered bacterial strain can be generated from a wild-type susceptible bacterial strain via a genetic engineering manner, which after the genetic engineering, is given mutation or antibiotic resistance gene to confer drug resistance. The genetic engineering can be conducted by a conventional method as known in the art, such as by a chromosome-mediated approach (e.g. mutating a gene in the chromosome of the strain to confer drug resistance) or a plasmid-mediated approach (e.g. adding a foreign gene to confer drug resistance in the strain). The genetically engineered bacterial strain can include one or more genetic changes based on one or more drug-resistant mechanisms selected form the group consisting of (i) decrease antibiotic permeability by loss of outer membrane proteins, (ii) pump out the antibiotics by overexpression of efflux pumps, (iii) eliminates or reduces binding of antibiotic by modification of antibiotic target or by acquirement of antibiotic-resistant target, and (iv) inactivate antibiotic by enzymatic cleavage or modification, and any combinations thereof. In some embodiments, the mutation or antibiotic resistance gene is selected from the group consisting of: ΔompK35, ΔompK36, ΔramR, GyrA S83I, GyrA S83L, GyrA S83F, GyrA S83Y, GyrA D87N, GyrA S80I, CTX-M-14, CTX-M-15, SHV-12, CMY-2, DHA-1-AmpR, KPC-2, KPC-3, IMP-8, NDM-1, VIM-1, OXA-48, QnrB, QnrS, AAC(6')-Ib-cr, AAC(6')-Ib-cr, AAC(3)-IId, AAC(3)-IVa, ANT(2")-Ia, ANT(3")-Ia, APH(3')-Ia, APH(3')-IIa, StrA-StrB, ArmA, RmtB, Tet(A), Tet(B), Tet(C), Tet(D), Tet(M), Sul1, Sul2, DfrA1, DfrA16, AdeR D20N, AdeR A91V, AdeR P116L, AdeS G30D, AdeS A94V, AdeS R152K, AdeS T153M, ParC G78C, ParC S80L, ParC S80W, ParC S80Y, ParC E84K, VEB-3, ADC-30, IMP-1, OXA-23, OXA-58, OXA-66, OXA-72, AAC(3)-IIa, APH(3')-VIa, and any combinations thereof. In some embodiments, the mutation or antibiotic resistance gene is preferably include genetic changes as many as possible which can be used to screen for a strong antimicrobial agent against multiple drug-resistant mechanisms.

The present invention provides a method for screening for an antibiotic agent. In particular, the method of the invention creates a genetically engineered bacterial strain from a wild-type susceptible bacterial strain via a genetic engineering manner, which after the genetic engineering, is given mutation or antibiotic resistance gene to confer drug resistance to a reference antibiotic based on one or more drug-resistant mechanisms; a test agent is then added to a culture of the wild-type susceptible bacterial strain and a culture of the genetically engineered bacterial strain to analyze for its activity against the wild-type susceptible bacterial strain and the genetically engineered bacterial strain, respectively, wherein the activity of the test agent against the bacterial strains can be expressed by a minimum inhibitory concentration (MIC) (also referring to a resistance level as described herein; typically, a higher MIC indicates a higher resistance level and a lower antimicrobial activity, and a lower MIC indicates a lower resistance level and a higher antimicrobial activity); and if the activity of the test agent against the genetically engineered bacterial strain is similar to that against the wild-type susceptible bacterial strain, the test agent is selected as a potential antimicrobial agent against the same species of the bacterial strain. In general, the antimicrobial activity of a test agent is expressed by MIC, which is preferably no more than 10 μg/ml, 5 μg/ml, 2.5 μg/ml, 1 μg/ml or 0.5 μg/ml.

Table A shows an embodiment of the method of the present invention.

|  | (1) Providing a wild-type (WT) susceptible bacterial strain (Preferably, the WT susceptible bacterial strain is susceptible to multiple antibiotics.) | (2) Creating a first genetically engineered bacterial strain having mutation 1 or antibiotic resistance gene 1 (ET1), from the wild-type (WT) susceptible bacterial strain via a genetically engineering technology to confer drug resistance. | (12) Creating a second genetically engineered bacterial strain having mutation 2 or antibiotic resistance gene 2 (ET2), from the wild-type (WT) susceptible bacterial strain via a genetically engineering technology to confer drug resistance. |
|---|---|---|---|
| A reference antibiotic | (1) the WT susceptible bacterial strain has a WT referenced resistance level to a reference antibiotic | (2) the first genetically engineered bacterial strain exhibits a ET1-referenced resistance level, which is higher than the WT-referenced resistance level, preferably by 1-fold, 2-fold, 3-fold, or 4-fold or more. | (12) the second genetically engineered bacterial strain exhibits a ET2-referenced resistance level, which is higher than the WT-referenced resistance level, preferably by 1-fold, 2-fold, 3-fold, or 4-fold or more. |
| Test 1 agent | (3) Culturing the WT susceptible bacterial strain in the presence of the Test 1 agent to obtain a WT-Test1 resistance level. | (4) Culturing the first genetically engineered bacterial strain with ET1 in the presence of the Test 1 agent to obtain a ET1-Test1 resistance level. (5) Obtaining a ET1-Test1 ratio of the ET1-Test1 resistance level to the WT-Test1 resistance level. (a ET1-Test1 ratio = the ET1-Test1 resistance level ÷ the WT-Test1 resistance level) (6) Determining if Test 1 agent is a potentially effective antimicrobial agent against the drug resistance associated with ET1 in the first genetically engineered bacterial strain based on the ET1-Test1 ratio. (Particularly, the Test 1 agent is determined as a potentially effective antimicrobial agent against the drug resistance associated with ET1 if the ET1-Test1 ratio is no more than 4) (Particularly, the first test agent is determined as a potentially effective antimicrobial agent against the drug resistance associated with ET1 if the ET1-Test1 resistance level, expressed by minimum inhibitory concentration (MIC), is no more than | (13) Culturing the second genetically engineered bacterial strain with ET2 in the presence of the Test 1 agent to obtain a ET2-Test1 resistance level. (14) Obtaining a ET2-Test1 ratio of the ET2-Test1 resistance level to the WT-Test1 resistance level is obtained. (a ET2-Test1 ratio = the ET2-Test1 resistance level ÷ the WT-Test1 resistance level) (15) Determining if Test 1 agent is an effective antimicrobial agent against the drug resistance associated with ET2 in the second genetically engineered bacterial strain based on the ET2-Test1 ratio. (Particularly, the Test 1 agent is determined as a potentially effective antimicrobial agent against the drug resistance associated with ET2 if the ET2-Test1 ratio is no more than 4) (Particularly, the first test agent is determined as a potentially effective antimicrobial agent against the drug resistance associated with ET2 if the ET2-Test1 resistance level, expressed by minimum inhibitory concentration (MIC), is no more than 10 μg/ml, 5 μg/ml, 2.5 μg/ml, |

-continued

| | | | |
|---|---|---|---|
| | | 10 µg/ml, 5 µg/ml, 2.5 µg/ml, 1 µg/ml or 0.5 µg/ml) | 1 µg/ml or 0.5 µg/ml) |
| | (16) Obtaining a first sum ratio value with respect to Test 1 agent by adding the ET1-Test1 ratio to the ET2-Test1 ratio | | |
| Test 2 agent | (7) (17) Culturing the WT susceptible bacterial strain in the presence of the Test 2 agent to obtain a WT-Test2 resistance level. | (8) (18) Culturing the first genetically engineered bacterial strain with ET1 in the presence of the Test 2 agent to obtain a ET1-Test2 resistance level. | (21) Culturing the second genetically engineered bacterial strain with ET2 in the presence of the Test 2 agent to obtain a ET2-Test2 resistance level. |
| | | (9) (19) Obtaining a ET1-Test2 ratio of the ET1-Test2 resistance level to the WT-Test2 resistance level. | (22) Obtaining a ET2-Test2 ratio of the ET2-Test2 resistance level to the WT-Test2 resistance level is obtained. |
| | | (a ET1-Test2 ratio = the ET1-Test2 resistance level ÷ the WT-Test2 resistance level) | (a ET2-Test2 ratio = the ET2-Test2 resistance level ÷ the WT-Test2 resistance level) |
| | | (10) (20) Determining if Test 2 agent is an effective antimicrobial agent against the drug resistance associated with ET1 in the first genetically engineered bacterial strain based on the ET1-Test2 ratio. | (23) Determining if Test 2 agent is an effective antimicrobial agent against the drug resistance associated with ET2 in the second genetically engineered bacterial strain based on the ET2-Test2 ratio. |
| | | (Particularly, the Test 2 agent is determined as an effective antimicrobial agent against the drug resistance associated with ET1 if the ET1-Test2 ratio is no more than 4) | (Particularly the Test 2 agent is determined as an effective antimicrobial agent against the drug resistance associated with ET2 if the ET2-Test2 ratio is no more than 4) |
| | | (Particularly, the second test agent is determined as a potentially effective antimicrobial agent against the drug resistance associated with ET1 if the ET1-Test2 resistance level, expressed by minimum inhibitory concentration (MIC), is no more than 10 µg/ml, 5 µg/ml, 2.5 µg/ml, 1 µg/ml or 0.5 µg/ml) | (Particularly, the second test agent is determined as a potentially effective antimicrobial agent against the drug resistance associated with ET2 if the ET2-Test2 resistance level, expressed by minimum inhibitory concentration (MIC), is no more than 10 µg/ml, 5 µg/ml, 2.5 µg/ml, 1 µg/ml or 0.5 µg/ml) |
| | (24) Obtaining a second sum ratio value with respect to Test 2 agent by adding the ET1-Test2 ratio to the ET2-Test2 ratio. | | |
| | (25) Ranking Test 1 agent and Test 2 agent for a preferable antimicrobial activity according to the first sum ratio value and the second sum ratio value, the lower the value, the higher the ranking. | | |
| | (11) Ranking Test 1 agent and Test 2 agent for a preferable antimicrobial activity according to the ET1-Test1 ratio and the ET1-Test2 ratio, the lower the ratio, the higher the ranking. | | |
| | (26) Ranking Test 1 agent and Test 2 agent for a preferable antimicrobial activity according to the ET2-Test1 ratio and the ET2-Test2 ratio, the lower the ratio, the higher the ranking. | | |

In certain embodiments, the method of the invention is to identify a potential agent with antimicrobial activity against multiple drug-resistance mechanisms.

In particular, the method of the present invention is advantageous to develop a platform technology to screen for a large number of agents for their antimicrobial activity. In addition, once a test agent is determined as a potentially antimicrobial agent in a first run of the process, it can be subjected to a subsequent run of the process by creating another genetically engineered bacterial strain with a new mutation or antibiotic resistance gene and repeating the steps of culturing, obtaining a resistance level and analyzing for its activity against the wild-type susceptible bacterial strain and the genetically engineered bacterial strain. The more times the process is conducted, the more accurate the results, and an agent thus selected by more runs of the process is more effective against various types of drug-resistant mechanisms.

The present invention will now be described more specifically with reference to the following examples, which are provided for the purpose of demonstration rather than limitation.

EXAMPLES

The system developed in the present study provides a platform technology for testing, screening, selecting and evaluating antibiotics using genetically engineered bacterial strains with individual or combined resistance mechanisms that were constructed from the fully susceptible clinical *K. pneumoniae* NVT1001 isolate. The chromosome-mediated resistance mechanisms that were constructed in this study are decreased antibiotic permeability, generated by deletion of the genes encoding the outer-membrane proteins OmpK35 and/or OmpK36;[7] active antibiotic export, generated by deletion of the ramR regulatory gene, which leads to overexpression of the AcrAB-TolC efflux pump (Tables 1);[8-11] and modification of quinolone target sites via gyrA and/or parC mutations.[12-15] Most plasmid-mediated mechanisms are specific to one kind of antibiotic group,[16] with this study focusing on β-lactams, quinolones, aminoglycosides, tetracyclines and folate pathway inhibitors. Because many kinds of resistance are conferred by combined resistance mechanisms in the clinical setting, mechanisms related to the same antibiotic group were combined. Testing antibiotics against these combined mechanisms can be used to further evaluate their antimicrobial activities.

TABLE 1

Relative transcription levels of the acrA, tolC, ramA and ramR in the genetically engineered strains in comparison with *K. pneumoniae* NVT1001[a]

| Strain | Gene transcription level (fold change)[b] | | | |
| --- | --- | --- | --- | --- |
| | acrA | tolC | ramA | ramR |
| NVT1001 | 1 | 1 | 1 | 1 |
| ΔramR[c] | 3.18 | 3.12 | 13.37 | 0 |
| ΔramR::ramR | 1.02 | 0.95 | 0.95 | 1 |

[a]The expression of acrAB and tolC is positively regulated by RamA, while RamR is a repressor that regulates ramA expression.[1] Previous study has found that after ramR disruption, the expression of acrA, tolC and ramA was increased 3.36-, 3.35- and 25.04-fold respectively,[2] while similar results can also obtained in this study.
[b]Boldface letter indicates at least a 2-fold change compared with that of *K. pneumoniae* NVT1001 and the results are the mean of three different experiments.
[c]ΔramR, ramR deletion strain of NVT1001; ΔramR::ramR, ramR-complemented strain of ΔramR strain.

In addition, Enterobacteriaceae, *Acinetobacter baumannii* and *Pseudomonas aeruginosa* have been identified by the WHO as three critical priority pathogens for the research and development of new antibiotics in 2017.[3] Given that the genetic background of *A. baumannii* is quite different from that of *K. pneumoniae*, specific resistance genes can be found in this pathogen. Therefore, the strategic system has been constructed by using *A. baumannii*.

This study includes generation of genetically engineered strains from a fully susceptible clinical isolate of *A. baumannii*. The chromosome-mediated resistance mechanisms that were constructed in this study are active antibiotic export, generated by mutation of the adeR or adeS regulatory gene, which leads to overexpression of the AdeABC efflux pump;41-46 and modification of quinolone target sites via gyrA and/or parC mutations.[47-54] Most plasmid-mediated mechanisms are specific to one kind of antibiotic group,[55] with this study focusing on β-lactams, aminoglycosides and tetracyclines. All of these genetically engineered *A. baumannii* strains are with clear and simple resistance mechanisms and their usability was evaluated via antimicrobial susceptibility testing in this study.

Prior to the present invention, no complete system is available for testing antibiotics against specific resistance mechanisms. This study generated genetically engineered strains with clear and simple resistance mechanisms and evaluated their usability via both in vitro and in vivo assays.

1. Materials and Methods 1.1 Concept and Approach to Engineer the Resistant Strains for Antibiotic Screening System.

To create the bacterial strains for antibiotic screening system, four approaches with different target related antibiotic resistance were used.

For construction of chromosomal mediated resistance, (i) decreasing penetration of antibiotic (knockout outer membrane protein genes ompK35 and ompK36 in *K. pneumoniae*),[7] (ii) increasing the expression of AcrAB-TolC (knockout regulatory gene ramR[8-11] or overexpression of the AdeABC efflux pump (mutation of the adeR or adeS regulatory gen)[41-46] and (iii) antibiotic target gene mutation were performed.[12-15,47-54] For plasmid mediated resistance, different class of plasmid mediated resistant genes including (i) β-lactam resistant genes, (ii) quinolones resistant genes, (iii) aminoglycosides resistant genes, (iv) tetracyclines resistant genes and (v) folate pathway inhibitor resistant genes[16] were individually transferred into susceptible strain. See, Tables 2 and 4.

1.2 Bacterial Strains and Plasmids 1.2.1 *K. pneumoniae* NVT1001

*K. pneumoniae* NVT1001, capsular serotype 1, is an isolate from a liver-abscess patient in Taiwan[17] that was fully susceptible to all antibiotics tested, except ampicillin. The NVT1001 strain was used to construct genetically engineered strains with the antibiotic resistance mechanisms that are shown in Table 2, and the revertants of the NVT1001 mutants constructed in this study are shown in Table 3.

TABLE 2

Antibiotic resistance mechanisms in fully susceptible clinical *K. pneumoniae* NVT1001

| Strain or plasmid | Genotype or description[a] | Major relevant antibiotic[b] |
| --- | --- | --- |
| Strain with chromosome-mediated resistance mechanism | | |
| ΔompK35 mutant | ΔompK35 | β-lactams |
| ΔompK36 mutant | ΔompK36 | β-lactams, Folate pathway inhibitors, Nitrofurans |
| ΔompK35/36 mutant | ΔompK35/36 | β-lactams, Folate pathway inhibitors, Fosfomycins, Nitrofurans |
| ΔramR mutant | ΔramR | β-lactams, Quinolones, Tetracyclines, Folate pathway inhibitors, Phenicols, Nitrofurans |
| ΔramRΔompK35 mutant | ΔramRΔompK35 | β-lactams, Quinolones, Tetracyclines, Folate pathway inhibitors, Phenicols, Nitrofurans |
| ΔramRΔompK36 mutant | ΔramRΔompK36 | β-lactams, Quinolones, Tetracyclines, Folate pathway inhibitors, Phenicols, Fosfomycins, Nitrofurans |

TABLE 2-continued

Antibiotic resistance mechanisms in fully susceptible clinical *K. pneumoniae* NVT1001

| Strain or plasmid | Genotype or description[a] | Major relevant antibiotic[b] |
|---|---|---|
| ΔramRΔompK35/36 mutant | ΔramRΔompK35/36 | β-lactams, Quinolones, Tetracyclines, Folate pathway inhibitors, Phenicols, Fosfomycins, Nitrofurans |
| S83I mutant | GyrA S83I | Quinolones |
| S83L mutant | GyrA S83L | Quinolones |
| S83F mutant | GyrA S83F | Quinolones |
| S83Y mutant | GyrA S83Y | Quinolones |
| D87N mutant | GyrA D87N | Quinolones |
| S80I mutant | ParC S80I | None |
| D87N/S80I mutant | GyrA D87N; ParC S80I | Quinolones |
| S83I/D87N mutant | GyrA S83I/D87N | Quinolones |
| S83L/D87N mutant | GyrA S83L/D87N | Quinolones |
| S83F/D87N mutant | GyrA S83F/D87N | Quinolones |
| S83Y/D87N mutant | GyrA S83Y/D87N | Quinolones |
| S83I/S80I mutant | GyrA S83I; ParC S80I | Quinolones |
| S83L/S80I mutant | GyrA S83L; ParC S80I | Quinolones |
| S83F/S80I mutant | GyrA S83F; ParC S80I | Quinolones |
| S83Y/S80I mutant | GyrA S83Y; ParC S80I | Quinolones |
| S83I/D87N/S80I mutant | GyrA S83I/D87N; ParC S80I | Quinolones |
| S83L/D87N/S80I mutant | GyrA S83L/D87N; ParC S80I | Quinolones |
| S83F/D87N/S80I mutant | GyrA S83F/D87N; ParC S80I | Quinolones |
| S83Y/D87N/S80I mutant | GyrA S83Y/D87N; ParC S80I | Quinolones |
| ΔramR/S83I mutant | ΔramR; GyrA S83I | β-lactams, Quinolones, Tetracyclines, Folate pathway inhibitors, Phenicols, Nitrofurans |
| ΔramR/S83I/S80I mutant | ΔramR; GyrA S83I; ParC S80I | β-lactams, Quinolones, Tetracyclines, Folate pathway inhibitors, Phenicols, Nitrofurans |
| ΔramR/S83I/D87N/S80I mutant | ΔramR; GyrA S83I/D87N; ParC S80I | β-lactams, Quinolones, Tetracyclines, Folate pathway inhibitors, Phenicols, Nitrofurans |
| Plasmid with plasmid-mediated resistance mechanism | | |
| p177/CTX-M-14 | $bla_{CTX-M-14}$ cloned into pACYC177 | β-lactams |
| p177/CTX-M-15 | $bla_{CTX-M-15}$ cloned into pACYC177 | β-lactams |
| p177/SHV-12 | $bla_{SHV-12}$ cloned into pACYC177 | β-lactams |
| p1771/CMY-2 | $bla_{CMY-2}$ cloned into pACYC177 | β-lactams |
| p177/DHA-1-AmpR | $bla_{DHA-1-AmpR}$ cloned into pACYC177 | β-lactams |
| p177/KPC-2 | $bla_{KPC-2}$ cloned into pACYC177 | β-lactams |
| p177/KPC-3 | $bla_{KPC-3}$ cloned into pACYC177 | β-lactams |
| p177/IMP-8 | $bla_{IMP-8}$ cloned into pACYC177 | β-lactams |
| p177/NDM-1 | $bla_{NDN-1}$ cloned into pACYC177 | β-lactams |
| p177/VIM-1 | $bla_{VIM-1}$ cloned into pACYC177 | β-lactams |
| p177/OXA-48 | $bla_{OXA-48}$ cloned into pACYC177 | β-lactams |
| p177/QnrB | qnrB cloned into pACYC177 | Quinolones |
| p177/QnrS | qnrS cloned into pACYC177 | Quinolones |
| p177/AAC(6')-Ib-cr | aac(6')-Ib-cr cloned into pACYC177 | Aminoglycosides, Quinolones |
| p184/AAC(6')-Ib-cr | aac(6')-Ib-cr cloned into pACYC184 | Aminoglycosides, Quinolones |
| p184/AAC(3)-IId | aac(3)-IId cloned into pACYC184 | Aminoglycosides |
| p184/AAC(3)-IVa | aac(3)-IVa cloned into pACYC184 | Aminoglycosides |
| p184/ANT(2″)-Ia | ant(2″)-Ia cloned into pACYC184 | Aminoglycosides |
| p184/ANT(3″)-Ia | ant(3″)-Ia cloned into pACYC184 | Aminoglycosides |
| p184/APH(3')-Ia | aph(3')-Ia cloned into pACYC184 | Aminoglycosides |
| p184/APH(3')-IIa | aph(3')-IIa cloned into pACYC184 | Aminoglycosides |
| p184/StrA-StrB | strA-strB cloned into pACYC184 | Aminoglycosides |
| p184/ArmA | armA cloned into pACYC184 | Aminoglycosides |
| p184/RmtB | rmtB cloned into pACYC184 | Aminoglycosides |
| p177/Tet(A) | tet(A) cloned into pACYC177 | Tetracyclines |
| p177/Tet(B) | tet(B) cloned into pACYC177 | Tetracyclines |
| p177/Tet(C) | tet(C) cloned into pACYC177 | Tetracyclines |
| p177/Tet(D) | tet(D) cloned into pACYC177 | Tetracyclines |
| p177/Tet(M) | tet(M) cloned into pACYC177 | Tetracyclines |
| p177/Sul1 | sul1 cloned into pACYC177 | Folate pathway inhibitors |
| p177/Sul2 | sul2 cloned into pACYC177 | Folate pathway inhibitors |

TABLE 2-continued

Antibiotic resistance mechanisms in fully susceptible clinical *K. pneumoniae* NVT1001

| Strain or plasmid | Genotype or description[a] | Major relevant antibiotic[b] |
|---|---|---|
| p177/DfrA1 | dfrA1 cloned into pACYC177 | Folate pathway inhibitors |
| p177/DfrA16 | dfrA16 cloned into pACYC177 | Folate pathway inhibitors |

[a]Amino acid replacements of GyrA or ParC are listed; Resistance genes of plasmid-mediated mechanisms were cloned into the low-copy-number plasmid pACYC177 or pACYC184.
[b]The antibiotics listed indicate a significant (≥4-fold) difference in the MICs of the NVT1001 strain and its genetically engineered strains in this study.

TABLE 3

Revertants of the NVT1001's mutants that were constructed in this study

| Strain | Genotype | Description |
|---|---|---|
| ΔramRΔompK35/36::ramR::ompK35/36 revertant | NVT1001 | ramR, ompK35 and/or ompK36 |
| ΔramRΔompK35/36::ramR::ompK36 revertant | ΔompK35 | restored strains of the |
| ΔramRΔompK35/36::ramR::ompK35 revertant | ΔompK36 | ΔramRΔompK35/36 mutant |
| ΔramRΔompK35/36::ramR revertant | ΔompK35/36 | |
| ΔramRΔompK35/36::ompK35/36 revertant | ΔramR | |
| ΔramRΔompK35/36::ompK36 revertant | ΔramRΔompK35 | |
| ΔramRΔompK35/36::ompK35 revertant | ΔramRΔompK36 | |
| S83I/D87N/S80I::I83S/N87D/I80S revertant | NVT1001 | GyrA S83/D87 and ParC S80 |
| S83L/D87N/S80I::L83S/N87D/I80S revertant | NVT1001 | restored strains of the |
| S83F/D87N/S80I::F83S/N87D/I80S revertant | NVT1001 | S83I/D87N/S80I, |
| S83Y/D87N/S80I::Y83S/N87D/I80S revertant | NVT1001 | S83L/D87N/S80I, |
| | | S83F/D87N/S80I or |
| | | S83Y/D87N/S80I mutant |
| S83I/D87N/S80I::N87D/I80S revertant | GyrA S83I | GyrA D87 and ParC S80 |
| S83L/D87N/S80I::N87D/I80S revertant | GyrA S83L | restored strains of the |
| S83F/D87N/S80I::N87D/I80S revertant | GyrA S83F | S83I/D87N/S80I, |
| S83Y/D87N/S80I::N87D/I80S revertant | GyrA S83Y | S83L/D87N/S80I, |
| | | S83F/D87N/S80I or |
| | | S83Y/D87N/S80I mutant |
| ΔramR/S83I/D87N/S80I::ramR/I83S/I80S revertant | GyrA D87N | ramR, GyrA S83, GyrA D87, |
| ΔramR/S83I/D87N/S80I::ramR/I83S/N87D revertant | ParC S80I | and/or ParC S80 restored |
| ΔramR/S83I/D87N/S80I::I83S/N87D/I80S revertant | ΔramR | strains of the |
| ΔramR/S83I/D87N/S80I::ramR/I83S revertant | GyrA D87N; ParC S80I | ΔramR/S83I/D87N/S80I mutant |
| S83I/D87N/S80I::I80S revertant | GyrA S83I/D87N | ParC S80 restored strains of |
| S83L/D87N/S80I::I80S revertant | GyrA S83L/D87N | the S83I/D87N/S80I, |
| S83F/D87N/S80I::I80S revertant | GyrA S83F/D87N | S83L/D87N/S80I, |
| S83Y/D87N/S80I::I80S revertant | GyrA S83Y/D87N | S83F/D87N/S80I or |
| | | S83Y/D87N/S80I mutant |
| S83I/D87N/S80I::N87D revertant | GyrA S83I; ParC S80I | GyrA D87 restored strains of |
| S83L/D87N/S80I::N87D revertant | GyrA S83L; ParC S80I | the S83I/D87N/S80I, |
| S83F/D87N/S80I::N87D revertant | GyrA S83F; ParC S80I | S83L/D87N/S80I, |
| S83Y/D87N/S80I::N87D revertant | GyrA S83Y; ParC S80I | S83F/D87N/S80I or |
| | | S83Y/D87N/S80I mutant |
| ΔramR/S83I/D87N/S80I::ramR/I83S/N87D/I80S revertant | NVT1001 | ramR, GyrA S83, GyrA D87 |
| ΔramR/S83I/D87N/S80I::N87D/I80S revertant | ΔramR; GyrA S83I | and/or ParC S80, restored |
| ΔramR/S83I/D87N/S80I::N87D revertant | ΔramR; GyrA S83I; ParC S80I | strains of the ΔramR/S83I/D87N/S80I mutant |

1.2.2 *A. baumannii* KW1

*A. baumannii* KW1 is a clinical isolate that was fully susceptible to antibiotics tested. The KW1 strain was used to construct genetically engineered strains with the antibiotic resistance mechanisms that are shown in Table 4. The plasmids pYMAb5 and pYMab5Tc are shuttle vectors able to replicate in *A. baumannii* and *Escherichia coli*, which carry a resistant determinant of kanamycin or tetracycline respectively. The two shuttle vectors were used to clone the resistance genes of the plasmid-mediated resistance mechanisms in this study (Table 4).

TABLE 4

Antibiotic resistance mechanisms in fully susceptible clinical *A. baumannii* KW1

| Strain or plasmid | Genotype or description[a] | Major relevant antibiotic[b] |
|---|---|---|
| Strain with chromosome-mediated resistance mechanism | | |
| D20N mutant | AdeR D20N | β-lactams, quinolones, aminoglycosides, tetracyclines |
| A91V mutant | AdeR A91V | β-lactams, quinolones, aminoglycosides, tetracyclines |
| P116L mutant | AdeR P116L | β-lactams, quinolones, aminoglycosides, tetracyclines |
| G30D mutant | AdeS G30D | β-lactams, quinolones, aminoglycosides, tetracyclines |
| A94V mutant | AdeS A94V | β-lactams, quinolones, aminoglycosides, tetracyclines |
| R152K mutant | AdeS R152K | β-lactams, quinolones, aminoglycosides, tetracyclines |
| T153M mutant | AdeS T153M | β-lactams, quinolones, aminoglycosides, tetracyclines |
| S83L mutant | GyrA S83L | quinolones |
| G78C mutant | ParC G78C | none |
| S80L mutant | ParC S80L | none |
| S80W mutant | ParC S80W | none |
| S80Y mutant | ParC S80Y | none |
| E84K mutant | ParC E84K | none |
| S83L/G78C mutant | GyrA S83L; ParC G78C | quinolones |
| S83L/S80L mutant | GyrA S83L; ParC S80L | quinolones |
| S83L/S80W mutant | GyrA S83L; ParC S80W | quinolones |
| S83L/S80Y mutant | GyrA S83L; ParC S80Y | quinolones |
| S83L/E84K mutant | GyrA S83L; ParC E84K | quinolones |
| Plasmid with plasmid-mediated resistance mechanism | | |
| pB5/CTX-M-15 | $bla_{CTX-M-15}$ cloned into pYMAb5 | β-lactams |
| pB5/VEB-3 | $bla_{VEB-3}$ cloned into pYMAb5 | β-lactams |
| pB5/ADC-30 | $bla_{ADC-30}$ cloned into pYMAb5 | β-lactams |
| pB5/IMP-1 | $bla_{IMP-1}$ cloned into pYMAb5 | β-lactams |
| pB5/NDM-1 | $bla_{NDM-1}$ cloned into pYMAb5 | β-lactams |
| pB5/VIM-1 | $bla_{VIM-1}$ cloned into pYMAb5 | β-lactams |
| pB5/OXA-23 | $bla_{OXA-23}$ cloned into pYMAb5 | β-lactams |
| pB5/OXA-58 | $bla_{OXA-58}$ cloned into pYMAb5 | β-lactams |
| pB5/OXA-66 | $bla_{OXA-66}$ cloned into pYMAb5 | β-lactams |
| pB5/OXA-72 | $bla_{OXA-72}$ cloned into pYMAb5 | β-lactams |
| pB5Tc/AAC(3)-IIa | aac(3)-IIa cloned into pYMAb5Tc | aminoglycosides |
| pB5Tc/ANT(2″)-Ia | ant(2″)-Ia cloned into pYMAb5Tc | aminoglycosides |
| pB5Tc/ANT(3″)-Ia | ant(3″)-Ia cloned into pYMAb5Tc | aminoglycosides |
| pB5Tc/APH(3′)-Ia | aph(3′)-Ia cloned into pYMAb5Tc | aminoglycosides |
| pB5Tc/APH(3′)-VIa | aph(3′)-VIa cloned into pYMAb5Tc | aminoglycosides |
| pB5Tc/ArmA | armA cloned into pYMAb5Tc | aminoglycosides |
| pB5/Tet(A) | tet(A) cloned into pYMAb5 | tetracyclines |

TABLE 4-continued

Antibiotic resistance mechanisms in fully susceptible clinical *A. baumannii* KW1

| Strain or plasmid | Genotype or description[a] | Major relevant antibiotic[b] |
|---|---|---|
| pB5/Tet(B) | tet(B) cloned into pYMAb5 | tetracyclines |
| pB5/Tet(M) | tet(M) cloned into pYMAb5 | tetracyclines |

[a]Amino acid replacement of AdeR, AdeS, GyrA or ParC are listed; resistance genes of plasmid-mediated mechanisms were clone into the shuttle vector pYMAb5 or pYMAb5Tc, which carries a resistant determinant of kanamycin or tetracycline respectively.
[b]The antibiotics listed indicate a ≥2-fold difference in the MICs for the KW1 strain and its genetically engineered strains in this study.

1.3 In-Frame Deletion Mutagenesis

The plasmid pUT-kmy, which consists of an R6K origin of replication, an mobRP4 origin of transfer, and a kanamycin resistance cassette,[18] was ligated with the sacB gene to generate the plasmid pUT-KB, which was then used to construct the mutants.[19] The plasmid pUT-KB is a suicide vector containing the counter-selection marker sacB, which originates from *Bacillus subtilis*.[20] When this gene is expressed via the integrated pUT-KB, it confers a sucrose-susceptibility phenotype, which enables positive selection with sucrose to detect loss of the vector.

Gene deletions in *K. pneumoniae* strain NVT1001 were constructed via in-frame deletion mutagenesis.[7] Briefly, two DNA fragments (approximately 1 kb in size) that flanked the regions to be deleted were amplified by PCR using specific primer pairs. The two gel-purified PCR products, containing complementary ends, were then mixed and amplified via overlap PCR.[21,22] The resulting PCR fragment (approximately 2 kb in size) was digested with restriction enzymes and then cloned into pUT-KB that had been similarly digested. For homologous recombination, each of the gene-deletion constructs in pUT-KB was transformed into *E. coli* S17-1 λpir[23] via electroporation and then mobilized into *K. pneumoniae* strain NVT1001 via conjugation. Single-crossover strains were selected from BIND (Brilliant green containing Inositol-Nitrate-Deoxycholate) plates supplemented with kanamycin (50 mg/L), as the growth of non-*K. pneumoniae* strains is effectively suppressed on BIND plates.[24] After the kanamycin-resistant transconjugants were selected, the insertions of the plasmids were verified via PCR using primer pairs that flanked the target genes. After incubation in 20 mL brain-heart infusion (BHI) broth for 6 hours at 37° C. in the absence of kanamycin, the fully grown cultures were spread onto LB agar plates supplemented with 10% sucrose. After the double crossover occurred, the sucrose-resistant and kanamycin-susceptible colonies were selected, and the gene deletions were confirmed via PCR.

1.4 Site-Directed Mutagenesis

DNA fragments of the entire gyrA and parC sequences along with their flanking regions were amplified from *K. pneumoniae* strain NVT1001 using PCR with specific primer pairs and then cloned into the plasmid pUT-KB. The QuikChange site-directed mutagenesis kit (Stratagene) was used to generate mutations in the gyrA and parC genes in the plasmid using the methods described by the manufacturer. For homologous recombination, plasmids containing mutations in the gyrA or parC gene were transformed into *E. coli* S17-1 λpir[23] via electroporation and mobilized into *K. pneumoniae* strain NVT1001 via conjugation. Single-crossover strains were selected from BIND plates supplemented with kanamycin (50 mg/L), as the growth of non-*K. pneumoniae* contaminants is suppressed on BIND plates.[24] After the kanamycin-resistant transconjugants were selected, the insertion of plasmids was verified via PCR. After incubation in 20 mL BHI broth for 6 hours at 37° C. in the absence of kanamycin, the fully grown cultures were spread onto LB agar plates supplemented with 10% sucrose. After the double crossover occurred, the sucrose-resistant and kanamycin-susceptible colonies were selected, and the gene mutations were confirmed via PCR.

Plasmid pUT-kmy, which consists of an R6K origin of replication, a mobRP4 origin of transfer, and a kanamycin resistant determinant,[56] was ligated with a sacB gene to generate plasmid pUT-KB for constructing mutants.[57] Plasmid pUT-KB is a suicide vector containing a counter-selection marker, sacB, which originates from *Bacillus subtilis*.[58] When this gene is expressed on the integrated pUT-KB, it confers a sucrose-sensitivity phenotype, which enables positive selection with sucrose to detect the loss of the vector.

DNA fragments of the entire adeR, adeS, gyrA and parC along with their flanking regions were amplified from *A. baumannii* KW1 using PCR with specific primer pairs and then cloned into plasmid pUT-KB. The QuikChange site-directed mutagenesis kit (Stratagene) was used to generate mutations in the adeR, adeS, gyrA and parC genes in the plasmids using the methods described by the manufacturer. For homologous recombination, plasmids containing mutations in the adeR, adeS, gyrA or parC gene were transformed into *E. coli* S17-1 λpir[23] via electroporation and mobilized into *A. baumannii* KW1 via conjugation. Single-crossover strains were selected from Luria-Bertani (LB) plates supplemented with cefotaxime (1 µg/ml) and kanamycin (50 m/ml), as the growth of non-*A. baumannii* contaminants is suppressed by cefotaxime (1 µg/ml). The kanamycin-resistant transconjugants were selected and the insertion of plasmids was verified via PCR. After incubation in 20 ml brain heart infusion (BHI) broth for 6 hours in the absence of kanamycin at 37° C., the fully grown cultures were spread onto LB plates supplemented with 10% sucrose. After the double crossover occurred, the sucrose-resistant and kanamycin-susceptible colonies were selected, and the gene mutations were confirmed via PCR.

1.5 Construction of Revertants

The allelic-exchange method was used to restore the wild-type gene in the *K. pneumoniae* NVT1001 mutants with constructed chromosome-mediated resistance mechanisms, as described by Tsai et al.[19] Briefly, a DNA fragment of the entire wild-type gene sequence along with flanking regions was amplified from *K. pneumoniae* NVT1001 using PCR with specific primers. The resulting PCR fragment was digested and then cloned into pUT-KB. For homologous recombination, this plasmid was transformed into *E. coli* S17-1 λpir[23] via electroporation and mobilized into the *K. pneumoniae* NVT1001 mutant via conjugation. Single-crossover strains were selected from BIND plates supplemented with kanamycin (50 mg/L), as the growth of non-*K. pneumoniae* strains is effectively suppressed on the BIND plates.[24] After the kanamycin-resistant transconjugants were selected, the insertion of the plasmid was verified via PCR. After incubation in 20 mL BHI broth for 6 hours at 37° C. in the absence of kanamycin, the fully grown cultures were spread onto LB agar plates supplemented with 10% sucrose. After the double crossover occurred, the sucrose-resistant and kanamycin-susceptible colonies were selected, and the restoration of the wild-type gene was confirmed via DNA sequencing.

1.6 Plasmid Construction and Transformation

DNA fragments of the resistance genes along with their flanking regions were amplified from clinical plasmids via PCR with specific primer pairs. The resulting PCR fragments were digested and then cloned into the plasmid pACYC177 or pACYC184. The resulting plasmids were then transformed into *K. pneumoniae* strain NVT1001 via electroporation. The recombinant bacteria were plated onto LB agar plates containing kanamycin (50 mg/L) or chloramphenicol (50 mg/L), and the presence of the cloned gene was confirmed via PCR and DNA sequencing.

DNA fragments of the resistance genes along with their flanking regions were amplified from clinical plasmids via PCR with specific primer pairs. The resulting PCR fragments were digested and then cloned into the plasmid pYMAb5 or pYMAb5Tc. The resulting plasmids were then transformed into *A. baumannii* KW1 via electroporation. The recombinant bacteria were plated onto LB agar plates containing kanamycin (50 μg/ml) or tetracycline (50 μg/ml), and the presence of the cloned gene was confirmed via PCR and DNA sequencing.

1.7 Antimicrobial Susceptibility Testing

The MICs of antibiotics were determined using the Etest (Biodisk AB, Sweden) according to the manufacturer's instructions. The MICs from the Etest, which fall between standard two-fold dilutions, were rounded up to the next highest two-fold value. The MICs of ceftazidime and cefotaxime against *K. pneumoniae* NVT1001 harbouring the pACYC177 plasmid with $bla_{OXA-48}$ were further determined using a broth microdilution test according to the recommendations of the CLSI,[25] and the results were interpreted according to the breakpoints established by the CLSI in 2017.[25] Meanwhile, due to the lack of CLSI breakpoints in 2016 and 2017, the results for cephalothin were interpreted according to the breakpoints established by the CLSI in 2015,[26] and the results for moxifloxacin were interpreted according to the breakpoints established by the EUCAST in 2017.[27]

1.8 Mouse Infection Model

Pathogen-free 6- to 8-week-old male BALB/c mice were obtained from the National Laboratory Animal Center (Taiwan) and maintained in the pathogen-free vivarium of the Laboratory Animal Center of National Defense Medical Center (Taiwan). *K. pneumoniae* NVT1001 harbouring the pACYC177 plasmid with $bla_{OXA-48}$ was cultured overnight at 37° C. in BHI broth and then diluted (1:100) in fresh BHI broth. The culture was incubated until the mid-exponential growth phase, and the cells were then washed once, resuspended in 0.85% sterile saline, and adjusted to the desired concentrations according to the $OD_{600}$ value. The concentrations were verified by plating the cells to determine viable counts. Six mice from each group were then injected intraperitoneally with 0.1 mL of the cell suspension containing twice the 90-100% lethal dose (LD90-100); this inoculum of $4 \times 10^3$ cfu/mouse was known to be 100% lethal within 7 days (data not shown). Meanwhile, antibiotic doses were prepared in 0.85% sterile saline. At 1 hour post-inoculation, antibiotic or 0.85% sterile saline alone was administered as a single subcutaneous injection with a volume of 0.3 mL per dose. The mice were then monitored daily for 7 days to measure survival. The ED50 was defined as the single dose giving protection to 50% of the test mice.

1.9 Quantitative real-time PCR (qRT-PCR)

*K. pneumoniae* strains were cultured in Mueller-Hinton broth (MHB) at 37° C. overnight, diluted (1:100) in fresh MHB, and then incubated at 37° C. until an OD600 of 0.8 (the mid-exponential growth phase) is reached. RNA was extracted using the RNeasy kit and treated with RNase-free DNase I according to the manufacturer's instructions (Qiagen). RNA yield and quality was measured using the NanoVue spectrophotometer (GE Healthcare Life Sciences). cDNAs were synthesized from 1 μg of RNA template using the Omniscript Reverse Transcriptase according to the manufacturer's instructions (Qiagen). Relative quantification of gene expression was performed using ABI PRISM 7900HT real-time PCR System (Applied Biosystems) with the Maxima SYBR Green qPCR Master Mix (Thermo Scientific) and primers listed in Table 5. Fold-change values were calculated after normalization of each gene to the 23S rRNA internal control,[3] using the comparative threshold method with the NVT1001 strain as the reference strain.

TABLE 5

Oligonucleotide primers for qRT-PCR in this study

| Primer | Sequence (5'-3') | Target | Reference |
|---|---|---|---|
| acrA-qF | ATGTGACGATAAACCGGCTC (SEQ ID NO: 1) | acrA | This study |
| acrA-qR | CTGGCAGTTCGGTGGTTATT (SEQ ID NO: 2) | | |
| tolC-qF | AACGGGCAGAACCAAATCGGC (SEQ ID NO: 3) | tolC | This study |
| tolC-qR | CGTTGATGCTGCTGATGGAGGC (SEQ ID NO: 4) | | |
| ramA-qF | TGATTCGCAACAGACTTTTACCCG (SEQ ID NO: 5) | ramA | This study |
| ramA-qR | GCGACTGTGGTTCTCTTTGCGGT (SEQ ID NO: 6) | | |
| ramR-qF | AGGATGAGTTGCTCAACGAG (SEQ ID NO: 7) | ramR | This study |

TABLE 5-continued

Oligonucleotide primers for qRT-PCR in this study

| Primer | Sequence (5'-3') | Target | Reference |
|---|---|---|---|
| ramR-qR | CCAGTCGATATAGCTGTTCCAG (SEQ ID NO: 8) | | |
| 23S-qF | GGTAGGGGAGCGTTCTGTAA (SEQ ID NO: 9) | 23S rRNA | 40 |
| 23S-qR | TCAGCATTCGCACTTCTGAT (SEQ ID NO: 10) | | |

2. Results 2.1 *K. pneumoniae* NVT1001

2.1.1 Porin Loss and Efflux-Pump Overexpression in Antibiotic Resistance

The MICs of antibiotics against chromosome-mediated resistance mechanisms, namely, OmpK35/36 loss and AcrAB-TolC overexpression (ΔramR), are shown in Table 6. These results demonstrate that OmpK35/36 loss is related to increased resistance to β-lactams, folate pathway inhibitors, fosfomycins and nitrofurans, whereas AcrAB-To1C overexpression (ΔramR) is associated with increased resistance to β-lactams, quinolones, tetracyclines, folate pathway inhibitors, phenicols and nitrofurans. The two resistance mechanisms alone or in combination had no significant (≥4-fold) effects on the MIC(s) of imipenem, aminoglycosides or polymyxins. The results shown above were further validated by testing the antimicrobial susceptibility of the revertant strains, and similar results were found when comparing the MIC of the wild-type strain NVT1001 or its mutant to the MIC of the revertant with the same genotype (Table 7).

TABLE 6

MICs of antibiotics against the chromosome-mediated resistance mechanisms, OmpK35/36 loss and AcrAB-TolC overexpression (ΔramR), in *K. pneumoniae* NVT1001

| Antibiotic group | Antibiotic[a] | MIC (mg/L)[b] | | | | | | | |
|---|---|---|---|---|---|---|---|---|---|
| | | WT[c] | Δ35 | Δ36 | Δ35/36 | ΔramR | ΔramR Δ35 | ΔramR Δ36 | ΔramR Δ35/36 |
| β-lactams | Aztreonam | 0.03 | 0.25 | 0.06 | 0.5 | 0.5 | 0.5 | 1 | 1 |
| | Piperacillin/TZB | 4 | 4 | 4 | 8 | 32 | 32 | 32 | 32 |
| | Ticarcillin/CLA | 4 | 4 | 4 | 16 | 8 | 16 | 16 | 8 |
| | Cephalothin | 8 | 8 | 16 | 256 | 64 | 64 | >256 | >256 |
| | Cefuroxime | 4 | 8 | 16 | 32 | 32 | 64 | >256 | 128 |
| | Cefoxitin | 4 | 4 | 16 | 128 | 64 | 64 | >256 | >256 |
| | Ceftazidime | 0.25 | 0.5 | 0.5 | 1 | 2 | 2 | 2 | 2 |
| | Cefotaxime | 0.06 | 0.125 | 0.25 | 2 | 1 | 1 | 4 | 4 |
| | Cefepime | 0.06 | 0.125 | 0.125 | 1 | 0.5 | 0.5 | 4 | 2 |
| | Ceftaroline | 0.25 | 0.25 | 0.5 | 1 | 1 | 1 | 4 | 4 |
| | Ertapenem | 0.015 | 0.03 | 0.03 | 2 | 0.125 | 0.125 | 4 | 4 |
| | Imipenem | 0.5 | 0.5 | 0.5 | 0.5 | 0.25 | 0.25 | 0.5 | 0.5 |
| | Meropenem | 0.06 | 0.06 | 0.06 | 0.5 | 0.06 | 0.06 | 2 | 2 |
| | Doripenem | 0.06 | 0.06 | 0.06 | 0.125 | 0.03 | 0.03 | 0.25 | 0.5 |
| Quinolones | Nalidixic acid | 4 | 8 | 4 | 8 | 32 | 64 | 32 | 32 |
| | Ciprofloxacin | 0.06 | 0.06 | 0.06 | 0.125 | 0.5 | 0.5 | 0.5 | 0.5 |
| | Norfloxacin | 0.25 | 0.25 | 0.25 | 0.5 | 2 | 2 | 2 | 2 |
| | Ofloxacin | 0.25 | 0.25 | 0.25 | 0.25 | 2 | 2 | 2 | 2 |
| | Levofloxacin | 0.06 | 0.125 | 0.125 | 0.125 | 1 | 1 | 1 | 1 |
| | Moxifloxacin | 0.125 | 0.125 | 0.06 | 0.125 | 1 | 1 | 1 | 1 |
| Aminoglycosides | Amikacin | 2 | 2 | 2 | 2 | 2 | 2 | 2 | 2 |
| | Gentamicin | 0.5 | 0.5 | 0.5 | 0.5 | 0.5 | 0.25 | 0.5 | 0.5 |
| | Kanamycin | 2 | 2 | 2 | 4 | 2 | 2 | 2 | 2 |
| | Netilmicin | 0.5 | 0.5 | 0.5 | 0.5 | 0.5 | 0.25 | 0.5 | 0.5 |
| | Spectinomycin | 16 | 16 | 16 | 16 | 16 | 16 | 16 | 16 |
| | Streptomycin | 2 | 4 | 4 | 4 | 2 | 2 | 4 | 4 |
| | Tobramycin | 0.5 | 0.5 | 0.5 | 0.5 | 0.5 | 0.5 | 0.5 | 1 |
| Tetracyclines | Tetracycline | 4 | 4 | 2 | 8 | 32 | 32 | 32 | 64 |
| | Doxycycline | 4 | 4 | 4 | 4 | 64 | 64 | 64 | 128 |
| | Minocycline | 4 | 4 | 4 | 4 | 64 | 128 | 128 | 128 |
| | Tigecycline | 1 | 1 | 1 | 1 | 8 | 8 | 8 | 8 |
| Folate pathway inhibitors | Trimethoprim | 2 | 2 | 2 | 2 | 8 | 8 | 16 | >32 |
| | Sulfamethoxazol | 256 | 256 | >1024 | >1024 | >1024 | >1024 | >1024 | >1024 |
| | SXT | 0.25 | 0.25 | 0.5 | 0.5 | 0.5 | 0.5 | 1 | 8 |
| Polymyxins | Polymyxin B | 2 | 2 | 2 | 2 | 1 | 1 | 2 | 1 |
| | Colistin | 1 | 1 | 1 | 1 | 1 | 1 | 1 | 1 |

TABLE 6-continued

MICs of antibiotics against the chromosome-mediated resistance mechanisms, OmpK35/36 loss
and AcrAB-TolC overexpression (ΔramR), in *K. pneumoniae* NVT1001

| Antibiotic group | Antibiotic[a] | MIC (mg/L)[b] | | | | | | | |
|---|---|---|---|---|---|---|---|---|---|
| | | WT[c] | Δ35 | Δ36 | Δ35/36 | ΔramR | ΔramR Δ35 | ΔramR Δ36 | ΔramR Δ35/36 |
| Phenicols | Chloramphenico | 8 | 8 | 8 | 8 | 128 | 128 | 128 | 128 |
| Fosfomycins | Fosfomycin | 128 | 128 | 256 | 512 | 64 | 128 | 512 | >1024 |
| Nitrofurans | Nitrofurantoin | 64 | 64 | >512 | >512 | 256 | 256 | >512 | >512 |

[a]TZB, tazobactam with a fixed concentration of 4 mg/L; CLA, clavulanic acid with a fixed concentration of 2 mg/L; SXT, trimethoprim/sulfamethoxazole (only the trimethoprim portion of the 1/19 drug ratio is displayed).
[b]Boldface numbers indicate a significant (≥4-fold) difference in the MICs of the NVT1001 strain and its mutants.
[c]WT, NVT1001; Δ35, ΔompK35 mutant; Δ36, ΔompK36 mutant; Δ35/36, ΔompK35/36 mutant; ΔramR, ΔramR mutant; ΔramRΔ35, ΔramRΔompK35 mutant; ΔramRΔ36, ΔramRΔompK36 mutant; ΔramRΔ35/36, ΔramRΔompK35/36 mutant.

TABLE 7

MICs of antibiotics against the ΔramRΔompK35/36 mutant and its revertants

| Antibiotic group | Antibiotic[a] | MIC (mg/L)[b] | | | | | | | |
|---|---|---|---|---|---|---|---|---|---|
| | | ΔramR Δ35/36::ramR:: 35/36[c] | ΔramR Δ35/36:: ramR::36 | ΔramR Δ35/36:: ramR::35 | ΔramR Δ35/36:: ramR | ΔramR Δ35/36:: 35/36 | ΔramR Δ35/ 36::36 | ΔramR Δ35/ 36::35 | ΔramR Δ35/36 |
| β-lactams | Aztreonam | 0.03 | 0.25 | 0.06 | 0.5 | 0.5 | 0.5 | 1 | 1 |
| | Piperacillin/TZB | 4 | 4 | 4 | 8 | 32 | 32 | 32 | 32 |
| | Ticarcillin/CLA | 4 | 4 | 4 | 16 | 16 | 16 | 16 | 8 |
| | Cephalothin | 8 | 8 | 32 | >256 | 64 | 128 | >256 | >256 |
| | Cefuroxime | 4 | 8 | 16 | 32 | 32 | 32 | >256 | 128 |
| | Cefoxitin | 4 | 8 | 16 | 64 | 64 | 64 | >256 | >256 |
| | Ceftazidime | 0.25 | 1 | 0.25 | 1 | 2 | 2 | 2 | 2 |
| | Cefotaxime | 0.06 | 0.125 | 0.25 | 2 | 1 | 1 | 4 | 4 |
| | Cefepime | 0.06 | 0.125 | 0.125 | 1 | 0.5 | 0.5 | 2 | 2 |
| | Ceftaroline | 0.25 | 0.5 | 0.5 | 1 | 1 | 1 | 4 | 4 |
| | Ertapenem | 0.015 | 0.03 | 0.03 | 1 | 0.125 | 0.125 | 4 | 4 |
| | Imipenem | 0.5 | 0.25 | 0.25 | 0.5 | 0.25 | 0.25 | 0.25 | 0.5 |
| | Meropenem | 0.125 | 0.125 | 0.125 | 0.5 | 0.06 | 0.06 | 2 | 2 |
| | Doripenem | 0.06 | 0.125 | 0.125 | 0.25 | 0.06 | 0.06 | 0.25 | 0.5 |
| Quinolones | Nalidixic acid | 8 | 8 | 8 | 8 | 64 | 64 | 32 | 32 |
| | Ciprofloxacin | 0.06 | 0.06 | 0.06 | 0.125 | 0.25 | 0.25 | 0.5 | 0.5 |
| | Norfloxacin | 0.25 | 0.25 | 0.25 | 0.5 | 2 | 2 | 2 | 2 |
| | Ofloxacin | 0.25 | 0.25 | 0.25 | 0.25 | 2 | 2 | 2 | 2 |
| | Levofloxacin | 0.06 | 0.125 | 0.06 | 0.125 | 0.5 | 0.5 | 1 | 1 |
| | Moxifloxacin | 0.125 | 0.125 | 0.06 | 0.06 | 0.5 | 0.5 | 1 | 1 |
| Tetracyclines | Tetracycline | 4 | 4 | 4 | 8 | 32 | 32 | 32 | 64 |
| | Doxycycline | 4 | 4 | 4 | 4 | 64 | 64 | 64 | 128 |
| | Minocycline | 4 | 4 | 4 | 4 | 128 | 128 | 128 | 128 |
| | Tigecycline | 1 | 1 | 1 | 1 | 8 | 8 | 8 | 8 |
| Folate pathway inhibitors | Trimethoprim | 2 | 2 | 2 | 2 | 8 | 8 | 8 | >32 |
| | Sulfamethoxazole | 256 | 256 | >1024 | >1024 | >1024 | >1024 | >1024 | >1024 |
| | SXT | 0.25 | 0.25 | 0.5 | 0.5 | 0.5 | 0.5 | 1 | 8 |
| Phenicols | Chloramphenicol | 4 | 8 | 4 | 8 | 64 | 64 | 128 | 128 |
| Fosomycins | Fosfomycin | 128 | 128 | 256 | 512 | 64 | 128 | 512 | >1024 |
| Nitrofurans | Nitrofurantoin | 64 | 64 | >512 | >512 | 256 | 256 | >512 | >512 |

[a]TZB, tazobactam with a fixed concentration of 4 mg/L; CLA, clavulanic acid with a fixed concentration of 2 mg/L; SXT, trimethoprim/sulfamethoxazole (only the trimethoprim portion of the 1/19 drug ratio is displayed).
[b]Boldface numbers indicate a significant (≥4-fold) difference in the MICs of the NVT1001 strain and its derived strains.
[c]ΔramRΔ35/36::ramR::35/36, ΔramRΔompK35/36::ramR::ompK35/36 revertant; ΔramRΔ35/36::ramR::36, ΔramRΔompK35/36::ramR::ompK36 revertant; ΔramRΔ35/36::ramR::35, ΔramRΔompK35/36::ramR::ompK35 revertant; ΔramRΔ35/36::ramR, ΔramRΔompK35/36::ramR revertant; ΔramRΔ35/36::35/36, ΔramRΔompK35/36::ompK35/36 revertant; ΔramRΔ35/36::36, ΔramRΔompK35/36::ompK36 revertant; ΔramRΔ35/36::35, ΔramRΔompK35/36::ompK35 revertant; ΔramR435/36, ΔramRΔompK35/36 mutant.

2.1.2 β-Lactams

The MICs of β-lactams against associated resistance mechanisms are shown in Tables 8 and 9. In particular, the MICs for extended-spectrum β-lactamases (ESBLs) and AmpC β-lactamases are shown in Table 8, while those for carbapenemases are shown in Table 9. The production of ESBLs when tested alone showed no significant (≥4-fold) effects on the MIC of piperacillin/tazobactam, cefoxitin, imipenem or doripenem, and the production of AmpC β-lactamases when tested alone showed no significant (≥4-fold) effects on the MIC of imipenem (Table 8). With or without ESBLs or AmpC β-lactamases, the strains with AcrAB-TolC overexpression (ΔramR) all showed no significant (≥4-fold) effects on the MIC of imipenem or doripenem (Table 8). The production of KPC-2 or KPC-3 alone could confer intermediate resistance to cefoxitin as well as resistance to the other tested β-lactams (Table 9). In addition, with or without OmpK35/36 loss and/or AcrAB-TolC overexpression (ΔramR), the IMP-8, NDM-1, VIM-1 and OXA-48 strains were susceptible to aztreonam (Table 9).

TABLE 8

MICs of β-lactams against the chromosome-mediated resistance mechanisms, OmpK35/36 loss and AcrAB-TolC overexpression (ΔramR), and/or the plasmid-mediated resistance mechanisms, extended-spectrum β-lactamase and AmpC β-lactamase, in *K. pneumoniae* NVT1001

| Supplemental plasmid and antibiotic[a] | MIC (mg/L)[b] | | | | | | | |
|---|---|---|---|---|---|---|---|---|
| | WT[c] | Δ35 | Δ36 | Δ35/36 | ΔramR | ΔramR Δ35 | ΔramR Δ36 | ΔramR Δ35/36 |
| No | | | | | | | | |
| Aztreonam | 0.03 | 0.25 | 0.06 | 0.5 | 0.5 | 0.5 | 1 | 1 |
| Piperacillin/TZB | 4 | 4 | 4 | 8 | 32 | 32 | 32 | 32 |
| Ticarcillin/CLA | 4 | 4 | 4 | 16 | 8 | 16 | 16 | 8 |
| Cephalothin | 8 | 8 | 16 | 256 | 64 | 64 | >256 | >256 |
| Cefuroxime | 4 | 8 | 16 | 32 | 32 | 64 | >256 | 128 |
| Cefoxitin | 4 | 4 | 16 | 128 | 64 | 64 | >256 | >256 |
| Ceftazidime | 0.25 | 0.5 | 0.5 | 1 | 2 | 2 | 2 | 2 |
| Cefotaxime | 0.06 | 0.125 | 0.25 | 2 | 1 | 1 | 4 | 4 |
| Cefepime | 0.06 | 0.125 | 0.125 | 1 | 0.5 | 0.5 | 4 | 2 |
| Ceftaroline | 0.25 | 0.25 | 0.5 | 1 | 1 | 1 | 4 | 4 |
| Ertapenem | 0.015 | 0.03 | 0.03 | 2 | 0.125 | 0.125 | 4 | 4 |
| Imipenem | 0.5 | 0.5 | 0.5 | 0.5 | 0.25 | 0.25 | 0.5 | 0.5 |
| Meropenem | 0.06 | 0.06 | 0.06 | 0.5 | 0.06 | 0.06 | 2 | 2 |
| Doripenem | 0.06 | 0.06 | 0.06 | 0.125 | 0.03 | 0.03 | 0.25 | 0.5 |
| CTX-M-14 | | | | | | | | |
| Aztreonam | 2 | 16 | 2 | 32 | 16 | 16 | 16 | 32 |
| Piperacillin/TZB | 4 | 8 | 8 | 16 | 32 | 32 | 32 | 64 |
| Ticarcillin/CLA | 32 | 64 | 64 | >256 | 64 | 64 | >256 | >256 |
| Cephalothin | >256 | >256 | >256 | >256 | >256 | >256 | >256 | >256 |
| Cefuroxime | >256 | >256 | >256 | >256 | >256 | >256 | >256 | >256 |
| Cefoxitin | 4 | 8 | 16 | 64 | 64 | 64 | >256 | >256 |
| Ceftazidime | 1 | 4 | 2 | 8 | 8 | 8 | 8 | 16 |
| Cefotaxime | 64 | 128 | >256 | >256 | 128 | 128 | >256 | >256 |
| Cefepime | 8 | 16 | 16 | 128 | 16 | 16 | 256 | 256 |
| Ceftaroline | 128 | >256 | >256 | >256 | >256 | >256 | >256 | >256 |
| Ertapenem | 0.125 | 0.25 | 0.25 | 8 | 0.25 | 0.25 | 16 | 16 |
| Imipenem | 0.5 | 0.5 | 0.5 | 1 | 0.25 | 0.25 | 0.5 | 0.5 |
| Meropenem | 0.06 | 0.125 | 0.125 | 2 | 0.125 | 0.125 | 2 | 2 |
| Doripenem | 0.125 | 0.125 | 0.125 | 1 | 0.06 | 0.06 | 0.5 | 0.5 |
| CTX-M-15 | | | | | | | | |
| Aztreonam | 256 | >256 | >256 | >256 | >256 | >256 | >256 | >256 |
| Piperacillin/TZB | 4 | 8 | 8 | >256 | 64 | 64 | >256 | >256 |
| Ticarcillin/CLA | 32 | 128 | 64 | >256 | 128 | >256 | >256 | >256 |
| Cephalothin | >256 | >256 | >256 | >256 | >256 | >256 | >256 | >256 |
| Cefuroxime | >256 | >256 | >256 | >256 | >256 | >256 | >256 | >256 |
| Cefoxitin | 4 | 8 | 16 | 64 | 64 | 64 | >256 | >256 |
| Ceftazidime | 64 | >256 | 64 | >256 | 256 | >256 | >256 | >256 |
| Cefotaxime | >256 | >256 | >256 | >256 | >256 | >256 | >256 | >256 |
| Cefepime | 64 | >256 | >256 | >256 | 256 | >256 | >256 | >256 |
| Ceftaroline | >256 | >256 | >256 | >256 | >256 | >256 | >256 | >256 |
| Ertapenem | 0.5 | 0.5 | 0.5 | >32 | 0.5 | 0.5 | >32 | >32 |
| Imipenem | 0.5 | 0.5 | 0.5 | 4 | 0.5 | 0.25 | 2 | 2 |
| Meropenem | 0.25 | 0.25 | 0.25 | 8 | 0.25 | 0.25 | 4 | 4 |
| Doripenem | 0.125 | 0.125 | 0.25 | 4 | 0.125 | 0.125 | 2 | 2 |
| SHV-12 | | | | | | | | |
| Aztreonam | 128 | >256 | 128 | >256 | >256 | >256 | >256 | >256 |
| Piperacillin/TZB | 4 | 4 | 4 | >256 | 64 | 32 | >256 | >256 |
| Ticarcillin/CLA | 32 | 128 | 64 | >256 | 256 | 256 | >256 | >256 |
| Cephalothin | >256 | >256 | >256 | >256 | >256 | >256 | >256 | >256 |
| Cefuroxime | 64 | 64 | 128 | >256 | 256 | 128 | >256 | >256 |
| Cefoxitin | 4 | 8 | 16 | 128 | 64 | 64 | >256 | >256 |
| Ceftazidime | 64 | >256 | 128 | >256 | >256 | >256 | >256 | >256 |
| Cefotaxime | 32 | 32 | 32 | >256 | 64 | 64 | 256 | 256 |
| Cefepime | 4 | 4 | 4 | 128 | 8 | 8 | 64 | 128 |
| Ceftaroline | 16 | 16 | 16 | 64 | 16 | 16 | 32 | 32 |
| Ertapenem | 0.06 | 0.06 | 0.06 | 4 | 0.125 | 0.125 | 4 | 4 |
| Imipenem | 0.5 | 0.5 | 0.5 | 1 | 0.25 | 0.25 | 0.5 | 1 |
| Meropenem | 0.125 | 0.125 | 0.125 | 1 | 0.06 | 0.06 | 1 | 2 |
| Doripenem | 0.125 | 0.125 | 0.125 | 1 | 0.06 | 0.06 | 0.5 | 0.5 |
| CMY-2 | | | | | | | | |
| Aztreonam | 64 | 128 | 64 | 256 | 64 | 64 | 64 | 64 |
| Piperacillin/TZB | >256 | >256 | >256 | >256 | 256 | 256 | >256 | >256 |
| Ticarcillin/CLA | >256 | >256 | >256 | >256 | >256 | >256 | >256 | >256 |
| Cephalothin | >256 | >256 | >256 | >256 | >256 | >256 | >256 | >256 |
| Cefuroxime | 256 | 256 | >256 | >256 | >256 | >256 | >256 | >256 |

TABLE 8-continued

MICs of β-lactams against the chromosome-mediated resistance mechanisms, OmpK35/36 loss and AcrAB-TolC overexpression (ΔramR), and/or the plasmid-mediated resistance mechanisms, extended-spectrum β-lactamase and AmpC β-lactamase, in *K. pneumoniae* NVT1001

| Supplemental plasmid and antibiotic[a] | MIC (mg/L)[b] | | | | | | | |
|---|---|---|---|---|---|---|---|---|
| | WT[c] | Δ35 | Δ36 | Δ35/36 | ΔramR | ΔramR Δ35 | ΔramR Δ36 | ΔramR Δ35/36 |
| Cefoxitin | >256 | >256 | >256 | >256 | >256 | >256 | >256 | >256 |
| Ceftazidime | >256 | >256 | >256 | >256 | >256 | >256 | >256 | >256 |
| Cefotaxime | 64 | 128 | >256 | >256 | 128 | 128 | >256 | >256 |
| Cefepime | 2 | 2 | 16 | 32 | 4 | 4 | 16 | 16 |
| Ceftaroline | 64 | 64 | 256 | >256 | 64 | 64 | 256 | 128 |
| Ertapenem | 1 | 1 | 4 | >32 | 1 | 1 | >32 | >32 |
| Imipenem | 1 | 1 | 4 | >32 | 1 | 1 | 32 | 32 |
| Meropenem | 0.25 | 0.25 | 2 | 16 | 0.25 | 0.25 | 8 | 8 |
| Doripenem | 0.25 | 0.25 | 1 | 8 | 0.125 | 0.125 | 4 | 4 |
| DHA-1-AmpR | | | | | | | | |
| Aztreonam | 1 | 8 | 1 | 16 | 4 | 4 | 8 | 8 |
| Piperacillin/TZB | 4 | 8 | 8 | >256 | 32 | 32 | 64 | 64 |
| Ticarcillin/CLA | 256 | >256 | >256 | >256 | >256 | >256 | >256 | >256 |
| Cephalothin | >256 | >256 | >256 | >256 | >256 | >256 | >256 | >256 |
| Cefuroxime | >256 | >256 | >256 | >256 | >256 | >256 | >256 | >256 |
| Cefoxitin | >256 | >256 | >256 | >256 | >256 | >256 | >256 | >256 |
| Ceftazidime | 16 | 128 | 32 | >256 | 64 | 64 | 64 | 128 |
| Cefotaxime | 8 | 16 | 16 | 64 | 16 | 16 | 64 | 64 |
| Cefepime | 0.125 | 0.25 | 0.25 | 1 | 0.5 | 0.5 | 4 | 4 |
| Ceftaroline | 8 | 8 | 8 | 16 | 8 | 8 | 16 | 16 |
| Ertapenem | 1 | 1 | 1 | >32 | 1 | 1 | >32 | >32 |
| Imipenem | 0.5 | 0.5 | 0.5 | 32 | 0.25 | 0.25 | 16 | 16 |
| Meropenem | 0.25 | 0.25 | 0.25 | 8 | 0.125 | 0.25 | 8 | 4 |
| Doripenem | 0.125 | 0.125 | 0.25 | 8 | 0.125 | 0.125 | 4 | 4 |

[a]No, no supplemental plasmid. The β-lactamase on the low-copy-number plasmid pACYC177 is shown, and the plasmid was transferred into *K. pneumoniae* NVT1001 and its mutants. The DHA-1 was cloned with its regulator AmpR. TZB, tazobactam with a fixed concentration of 4 mg/L; CLA, clavulanic acid with a fixed concentration of 2 mg/L.
[b]Boldface numbers indicate a significant (≥4-fold) difference in the MICs of the NVT1001 strain and its derived strains, while no significant (≥4-fold) differences in the MICs of the NVT1001 with or without plasmid pACYC177 alone (data not shown).
[c]WT, NVT1001; Δ35, ΔompK35 mutant; Δ36, ΔompK36 mutant; Δ35/36, ΔompK35/36 mutant; ΔramR, ΔramR mutant; ΔramRΔ35, ΔramRΔompK35 mutant; ΔramRΔ36, ΔramRΔompK36 mutant; ΔramRΔ35/36, ΔramRΔompK35/36 mutant.

TABLE 9

MICs of β-lactams against the chromosome-mediated resistance mechanisms, OmpK35/36 loss and AcrAB-TolC overexpression (ΔramR), and/or the plasmid-mediated resistance mechanism, carbapenemase, in *K. pneumoniae* NVT1001

| Supplemental plasmid and antibiotic[a] | MIC (mg/L)[b] | | | | | | | |
|---|---|---|---|---|---|---|---|---|
| | WT[c] | Δ35 | Δ36 | Δ35/36 | ΔramR | ΔramR Δ35 | ΔramR Δ36 | ΔramR Δ35/36 |
| No | | | | | | | | |
| Aztreonam | 0.03 | 0.25 | 0.06 | 0.5 | 0.5 | 0.5 | 1 | 1 |
| Piperacillin/TZB | 4 | 4 | 4 | 8 | 32 | 32 | 32 | 32 |
| Ticarcillin/CLA | 4 | 4 | 4 | 16 | 8 | 16 | 16 | 8 |
| Cephalothin | 8 | 8 | 16 | 256 | 64 | 64 | >256 | >256 |
| Cefuroxime | 4 | 8 | 16 | 32 | 32 | 64 | >256 | 128 |
| Cefoxitin | 4 | 4 | 16 | 128 | 64 | 64 | >256 | >256 |
| Ceftazidime | 0.25 | 0.5 | 0.5 | 1 | 2 | 2 | 2 | 2 |
| Cefotaxime | 0.06 | 0.125 | 0.25 | 2 | 1 | 1 | 4 | 4 |
| Cefepime | 0.06 | 0.125 | 0.125 | 1 | 0.5 | 0.5 | 4 | 2 |
| Ceftaroline | 0.25 | 0.25 | 0.5 | 1 | 1 | 1 | 4 | 4 |
| Ertapenem | 0.015 | 0.03 | 0.03 | 2 | 0.125 | 0.125 | 4 | 4 |
| Imipenem | 0.5 | 0.5 | 0.5 | 0.5 | 0.25 | 0.25 | 0.5 | 0.5 |
| Meropenem | 0.06 | 0.06 | 0.06 | 0.5 | 0.06 | 0.06 | 2 | 2 |
| Doripenem | 0.06 | 0.06 | 0.06 | 0.125 | 0.03 | 0.03 | 0.25 | 0.5 |
| KPC-2 | | | | | | | | |
| Aztreonam | >256 | >256 | 256 | >256 | >256 | >256 | >256 | >256 |
| Piperacillin/TZB >256 | >256 | >256 | >256 | >256 | >256 | >256 | >256 | |
| Ticarcillin/CLA | >256 | >256 | >256 | >256 | >256 | >256 | >256 | >256 |
| Cephalothin | >256 | >256 | >256 | >256 | >256 | >256 | >256 | >256 |
| Cefuroxime | >256 | >256 | >256 | >256 | >256 | >256 | >256 | >256 |
| Cefoxitin | 16 | 32 | 64 | >256 | 128 | 128 | >256 | >256 |
| Ceftazidime | 16 | 64 | 32 | 256 | 128 | 128 | 128 | 128 |
| Cefotaxime | 128 | 256 | 256 | >256 | 256 | 256 | >256 | >256 |

TABLE 9-continued

MICs of β-lactams against the chromosome-mediated resistance mechanisms, OmpK35/36 loss and AcrAB-TolC overexpression (ΔramR), and/or the plasmid-mediated resistance mechanism, carbapenemase, in *K. pneumoniae* NVT1001

| Supplemental plasmid and antibiotic[a] | MIC (mg/L)[b] | | | | | | | |
|---|---|---|---|---|---|---|---|---|
| | WT[c] | Δ35 | Δ36 | Δ35/36 | ΔramR | ΔramR Δ35 | ΔramR Δ36 | ΔramR Δ35/36 |
| Cefepime | 64 | 64 | 64 | >256 | 64 | 64 | >256 | >256 |
| Ceftaroline | 256 | >256 | >256 | >256 | >256 | >256 | >256 | >256 |
| Ertapenem | 32 | 32 | 32 | >32 | >32 | >32 | >32 | >32 |
| Imipenem | >32 | >32 | >32 | >32 | >32 | >32 | >32 | >32 |
| Meropenem | 32 | >32 | >32 | >32 | 32 | >32 | >32 | >32 |
| Doripenem | 16 | 32 | >32 | >32 | 16 | 32 | >32 | >32 |
| KPC-3 | | | | | | | | |
| Aztreonam | >256 | >256 | >256 | >256 | >256 | >256 | >256 | >256 |
| Piperacillin/TZB | >256 | >256 | >256 | >256 | >256 | >256 | >256 | >256 |
| Ticarcillin/CLA | >256 | >256 | >256 | >256 | >256 | >256 | >256 | >256 |
| Cephalothin | >256 | >256 | >256 | >256 | >256 | >256 | >256 | >256 |
| Cefuroxime | >256 | >256 | >256 | >256 | >256 | >256 | >256 | >256 |
| Cefoxitin | 16 | 32 | 64 | >256 | 128 | 128 | >256 | >256 |
| Ceftazidime | 128 | >256 | 128 | >256 | >256 | >256 | >256 | >256 |
| Cefotaxime | 128 | 256 | 256 | >256 | 256 | 256 | >256 | >256 |
| Cefepime | 128 | 128 | 256 | >256 | 128 | 128 | >256 | >256 |
| Ceftaroline | 256 | 256 | >256 | >256 | 256 | 256 | >256 | >256 |
| Ertapenem | 32 | 32 | 32 | >32 | 32 | 32 | >32 | >32 |
| Imipenem | 32 | >32 | >32 | >32 | 32 | 32 | >32 | >32 |
| Meropenem | 16 | 32 | >32 | >32 | 32 | >32 | >32 | >32 |
| Doripenem | 8 | 32 | >32 | >32 | 16 | 32 | >32 | >32 |
| IMP-8 | | | | | | | | |
| Aztreonam | 0.06 | 0.25 | 0.06 | 0.5 | 0.5 | 0.5 | 0.5 | 0.5 |
| Piperacillin/TZB | 16 | 16 | 16 | 64 | 32 | 64 | 64 | 64 |
| Ticarcillin/CLA | >256 | >256 | >256 | >256 | >256 | >256 | >256 | >256 |
| Cephalothin | >256 | >256 | >256 | >256 | >256 | >256 | >256 | >256 |
| Cefuroxime | >256 | >256 | >256 | >256 | >256 | >256 | >256 | >256 |
| Cefoxitin | >256 | >256 | >256 | >256 | >256 | >256 | >256 | >256 |
| Ceftazidime | >256 | >256 | >256 | >256 | >256 | >256 | >256 | >256 |
| Cefotaxime | 64 | 128 | 256 | >256 | 128 | 128 | 256 | 256 |
| Cefepime | 16 | 32 | 64 | >256 | 32 | 64 | 128 | 128 |
| Ceftaroline | 64 | 64 | 64 | >256 | 32 | 64 | 64 | 128 |
| Ertapenem | 2 | 4 | 2 | >32 | 4 | 4 | >32 | >32 |
| Imipenem | 4 | 4 | 8 | >32 | 4 | 4 | >32 | >32 |
| Meropenem | 2 | 1 | 2 | >32 | 2 | 2 | >32 | >32 |
| Doripenem | 1 | 2 | 2 | >32 | 1 | 2 | 32 | 32 |
| NDM-1 | | | | | | | | |
| Aztreonam | 0.06 | 0.25 | 0.06 | 0.5 | 0.5 | 0.5 | 0.5 | 0.5 |
| Piperacillin/TZB | >256 | >256 | >256 | >256 | >256 | >256 | >256 | >256 |
| Ticarcillin/CLA | >256 | >256 | >256 | >256 | >256 | >256 | >256 | >256 |
| Cephalothin | >256 | >256 | >256 | >256 | >256 | >256 | >256 | >256 |
| Cefuroxime | >256 | >256 | >256 | >256 | >256 | >256 | >256 | >256 |
| Cefoxitin | >256 | >256 | >256 | >256 | >256 | >256 | >256 | >256 |
| Ceftazidime | >256 | >256 | >256 | >256 | >256 | >256 | >256 | >256 |
| Cefotaxime | 256 | 256 | >256 | >256 | >256 | >256 | >256 | >256 |
| Cefepime | 32 | 128 | >256 | >256 | >256 | 256 | >256 | >256 |
| Ceftaroline | >256 | >256 | >256 | >256 | >256 | >256 | >256 | >256 |
| Ertapenem | 32 | >32 | >32 | >32 | >32 | >32 | >32 | >32 |
| Imipenem | >32 | >32 | >32 | >32 | >32 | >32 | >32 | >32 |
| Meropenem | 32 | 32 | >32 | >32 | 32 | 32 | >32 | >32 |
| Doripenem | 16 | 32 | >32 | >32 | 32 | 32 | >32 | >32 |
| VIM-1 | | | | | | | | |
| Aztreonam | 0.06 | 0.25 | 0.06 | 0.5 | 0.5 | 0.5 | 1 | 1 |
| Piperacillin/TZB | >256 | >256 | >256 | >256 | >256 | >256 | >256 | >256 |
| Ticarcillin/CLA | >256 | >256 | >256 | >256 | >256 | >256 | >256 | >256 |
| Cephalothin | >256 | >256 | >256 | >256 | >256 | >256 | >256 | >256 |
| Cefuroxime | >256 | >256 | >256 | >256 | >256 | >256 | >256 | >256 |
| Cefoxitin | >256 | >256 | >256 | >256 | >256 | >256 | >256 | >256 |
| Ceftazidime | >256 | >256 | >256 | >256 | >256 | >256 | >256 | >256 |
| Cefotaxime | >256 | >256 | >256 | >256 | >256 | >256 | >256 | >256 |
| Cefepime | 128 | 256 | >256 | >256 | >256 | >256 | >256 | >256 |
| Ceftaroline | 256 | >256 | >256 | >256 | >256 | >256 | >256 | >256 |
| Ertapenem | 2 | 4 | 2 | >32 | 4 | 4 | >32 | >32 |
| Imipenem | 16 | 32 | >32 | >32 | 16 | 16 | >32 | >32 |

TABLE 9-continued

MICs of β-lactams against the chromosome-mediated resistance mechanisms, OmpK35/36 loss and AcrAB-TolC overexpression (ΔramR), and/or the plasmid-mediated resistance mechanism, carbapenemase, in *K. pneumoniae* NVT1001

| Supplemental plasmid and antibiotic[a] | MIC (mg/L)[b] | | | | | | | |
|---|---|---|---|---|---|---|---|---|
| | WT[c] | Δ35 | Δ36 | Δ35/36 | ΔramR | ΔramR Δ35 | ΔramR Δ36 | ΔramR Δ35/36 |
| Meropenem | 16 | >32 | >32 | >32 | >32 | 32 | >32 | >32 |
| Doripenem | 16 | 32 | >32 | >32 | 32 | 32 | >32 | >32 |
| OXA-48 | | | | | | | | |
| Aztreonam | 0.06 | 0.25 | 0.125 | 0.5 | 0.5 | 0.5 | 0.5 | 0.5 |
| Piperacillin/TZB | >256 | >256 | >256 | >256 | >256 | >256 | >256 | >256 |
| Ticarcillin/CLA | >256 | >256 | >256 | >256 | >256 | >256 | >256 | >256 |
| Cephalothin | 256 | 256 | >256 | >256 | >256 | >256 | >256 | >256 |
| Cefuroxime | 8 | 16 | 32 | 128 | 64 | 64 | >256 | >256 |
| Cefoxitin | 4 | 8 | 16 | 128 | 128 | 64 | >256 | >256 |
| Ceftazidime | 0.5 | 1 | 0.5 | 2 | 2 | 2 | 2 | 2 |
| Cefotaxime | 2 | 4 | 16 | 32 | 4 | 4 | 32 | 32 |
| Cefepime | 0.5 | 1 | 1 | 8 | 1 | 1 | 8 | 8 |
| Ceftaroline | 8 | 8 | 8 | 32 | 8 | 8 | 8 | 16 |
| Ertapenem | 4 | 8 | 8 | >32 | 8 | 8 | >32 | >32 |
| Imipenem | 4 | 4 | 8 | >32 | 4 | 4 | >32 | >32 |
| Meropenem | 2 | 2 | 8 | >32 | 2 | 2 | >32 | >32 |
| Doripenem | 2 | 2 | 8 | >32 | 2 | 1 | >32 | >32 |

[a]No, no supplemental plasmid. The carbapenemase on the low-copy-number plasmid pACYC177 is shown, and the plasmid was transferred into *K. pneumoniae* NVT1001 and its mutants. TZB, tazobactam with a fixed concentration of 4 mg/L; CLA, clavulanic acid with a fixed concentration of 2 mg/L.
[b]Boldface numbers indicate a significant (≥4-fold) difference in the MICs of the NVT1001 strain and its derived strains, while no significant (≥4-fold) differences in the MICs of the NVT1001 with or without plasmid pACYC177 alone (data not shown).
[c]WT, NVT1001; Δ35, ΔompK35 mutant; Δ36, ΔompK36 mutant; Δ35/36, ΔompK35/36 mutant; ΔramR, ΔramR mutant; ΔramRΔ35, ΔramRΔompK35 mutant; ΔramRΔ36, ΔramRΔompK36 mutant; ΔramRΔ35/36, ΔramRΔompK35/36 mutant.

2.1.3 Quinolones

The MICs of quinolones against chromosome-mediated resistance mechanisms are shown in Table 10. Strains with a single mutation at GyrA (S83I, S83L, S83F, S83Y or D87N) or with AcrAB-TolC overexpression (ΔramR) showed significant (≥4-fold) increases in the MICs of all quinolones tested (Table 5). In contrast, the single mutation at ParC (S80I) showed no significant (≥4-fold) effects on the MIC of any of the quinolones tested, whereas significant (≥4-fold) increases in the MICs of quinolones were observed for the S83I, S83L, S83F, S83Y, S83I/D87N, S83L/D87N, S83F/D87N, S83Y/D87N and ΔramR/S83I mutants (Table 10). The results shown above were further validated by testing the antimicrobial susceptibility of the revertant strains, and similar results were found when comparing the MIC of the wild-type strain NVT1001 or its mutant to the MIC of the revertant with the same genotype (Table 11).

The MICs of quinolones against plasmid-mediated resistance mechanisms with or without combination with chromosome-mediated resistance mechanisms are shown in Table 6. In contrast to QnrB or QnrS, strains with AAC(6')-Ib-cr exhibited a significant (≥4-fold) increase in the MIC of only ciprofloxacin or norfloxacin (Table 12). Even without plasmid-mediated resistance mechanisms, strains with the GyrA (S83I) mutation and AcrAB-TolC overexpression (ΔramR) could resist all tested quinolones (Table 12).

TABLE 10

MICs of quinolones against the chromosome-mediated resistance mechanisms, GyrA/ParC mutations and AcrAB-TolC overexpression (ΔramR), in *K. pneumoniae* NVT1001

| Strain | MIC (mg/L)[a] | | | | | |
|---|---|---|---|---|---|---|
| | NAL[b] | CIP | NOR | OFX | LVX | MXF |
| NVT1001 | 4 | 0.06 | 0.25 | 0.25 | 0.06 | 0.125 |
| S83I mutant | >256 | 0.5 | 2 | 2 | 0.5 | 1 |
| S83L mutant | >256 | 0.5 | 2 | 2 | 0.5 | 0.5 |
| S83F mutant | >256 | 0.5 | 2 | 2 | 0.5 | 0.5 |
| S83Y mutant | >256 | 0.5 | 2 | 2 | 0.5 | 0.5 |
| D87N mutant | >256 | 0.25 | 2 | 1 | 0.5 | 0.5 |
| S80I mutant | 8 | 0.03 | 0.25 | 0.25 | 0.125 | 0.25 |
| ΔramR mutant | 32 | 0.5 | 2 | 2 | 1 | 1 |
| D87N/S80I mutant | >256 | 0.5 | 2 | 1 | 0.5 | 1 |
| S83I/D87N mutant | >256 | 0.5 | 2 | 2 | 1 | 1 |
| S83L/D87N mutant | >256 | 0.5 | 2 | 2 | 0.5 | 0.5 |
| S83F/D87N mutant | >256 | 0.5 | 2 | 2 | 0.5 | 0.5 |
| S83Y/D87N mutant | >256 | 0.5 | 2 | 2 | 0.5 | 0.5 |
| S83I/S80I mutant | >256 | 4 | 16 | 4 | 2 | 8 |
| S83L/S80I mutant | >256 | 1 | 8 | 4 | 1 | 2 |
| S83F/S80I mutant | >256 | 0.5 | 8 | 2 | 0.5 | 1 |
| S83Y/S80I mutant | >256 | 0.5 | 8 | 2 | 1 | 1 |
| S83I/D87N/S80I mutant | >256 | 32 | 64 | 32 | 8 | >32 |
| S83L/D87N/S80I mutant | >256 | 32 | 64 | 32 | 8 | 32 |
| S83F/D87N/S80I mutant | >256 | 32 | 32 | 16 | 8 | 32 |
| S83Y/D87N/S80I mutant | >256 | 16 | 32 | 16 | 4 | 32 |
| ΔramR/S83I mutant | >256 | 4 | 8 | >32 | 16 | 8 |
| ΔramR/S83I/S80I mutant | >256 | >32 | 128 | >32 | >32 | >32 |
| ΔramR/S83I/D87N/S80I mutant | >256 | >32 | >256 | >32 | >32 | >32 |

[a]Boldface numbers indicate a significant (≥4-fold) difference in the MICs of the NVT1001 strain and its mutants.
[b]NAL, nalidixic acid; CIP, ciprofloxacin; NOR, norfloxacin; OFX, ofloxacin; LVX, levofloxacin; MXF, moxifloxacin.

TABLE 11

MICs of quinolones against the gyrA/parC and gyrA/parC/ramR mutants, and their revertants

| Strain | NAL[b] | CIP | NOR | OFX | LVX | MXF |
|---|---|---|---|---|---|---|
| S83I/D87N/S80I::I83S/N87D/I80S revertant | 4 | 0.06 | 0.25 | 0.25 | 0.06 | 0.125 |
| S83L/D87N/S80I::L83S/N87D/I80S revertant | 4 | 0.06 | 0.25 | 0.25 | 0.06 | 0.125 |
| S83F/D87N/S80I::F83S/N87D/I80S revertant | 4 | 0.03 | 0.25 | 0.25 | 0.06 | 0.125 |
| S83Y/D87N/S80I::Y83S/N87D/I80S revertant | 8 | 0.03 | 0.25 | 0.25 | 0.06 | 0.125 |
| S83I/D87N/S80I::N87D/I80S revertant | >256 | 0.5 | 2 | 2 | 1 | 1 |
| S83L/D87N/S80I::N87D/I80S revertant | >256 | 0.5 | 2 | 2 | 1 | 0.5 |
| S83F/D87N/S80I::N87D/I80S revertant | >256 | 0.5 | 2 | 2 | 0.5 | 0.5 |
| S83Y/D87N/S80I::N87D/I80S revertant | >256 | 0.5 | 2 | 2 | 0.5 | 0.5 |
| ΔramR/S83I/D87N/S80I:: ramR/I83S/I80S revertant | >256 | 0.25 | 1 | 1 | 0.5 | 0.5 |
| ΔramR/S83I/D87N/S80I:: ramR/I83S/N87D revertant | 8 | 0.06 | 0.25 | 0.25 | 0.06 | 0.25 |
| ΔramR/S83I/D87N/S80I::I83S/N87D/I80S revertant | 32 | 0.25 | 2 | 2 | 1 | 1 |
| ΔramR/S83I/D87N/S80I:: ramR/I83S revertant | >256 | 0.5 | 2 | 1 | 0.5 | 1 |
| S83I/D87N/S80I::I80S revertant | >256 | 0.5 | 2 | 2 | 1 | 1 |
| S83L/D87N/S80I::I80S revertant | >256 | 0.5 | 2 | 2 | 1 | 1 |
| S83F/D87N/S80I::I80S revertant | >256 | 0.5 | 2 | 2 | 0.5 | 1 |
| S83Y/D87N/S80I::I80S revertant | >256 | 0.5 | 2 | 2 | 0.5 | 0.5 |
| S83I/D87N/S80I::N87D revertant | >256 | 4 | 16 | 8 | 4 | 4 |
| S83L/D87N/S80I::N87D revertant | >256 | 2 | 8 | 4 | 2 | 1 |
| S83F/D87N/S80I::N87D revertant | >256 | 1 | 4 | 4 | 1 | 0.5 |
| S83Y/D87N/S80I::N87D revertant | >256 | 1 | 4 | 4 | 1 | 0.5 |
| S83I/D87N/S80I mutant | >256 | 32 | 64 | 32 | 8 | >32 |
| S83L/D87N/S80I mutant | >256 | 32 | 64 | 32 | 8 | 32 |
| S83F/D87N/S80I mutant | >256 | 32 | 32 | 16 | 8 | 32 |
| S83Y/D87N/S80I mutant | >256 | 16 | 32 | 16 | 4 | 32 |
| ΔramR/S83I/D87N/S80I::ramR/I83S/N87D/I80S | 8 | 0.06 | 0.25 | 0.25 | 0.06 | 0.125 |
| ΔramR/S83I/D87N/S80I::N87D/I80S revertant | >256 | 4 | 8 | >32 | 8 | 8 |
| ΔramR/S83I/D87N/S80I::N87D revertant | >256 | >32 | 128 | >32 | >32 | >32 |
| ΔramR/S83I/D87N/S80I mutant | >256 | >32 | >256 | >32 | >32 | >32 |

[a]Boldface numbers indicate a significant (≥4-fold) difference in the MICs of the NVT1001 strain and its derived strains.
[b]NAL, nalidixic acid; CIP, ciprofloxacin; NOR, norfloxacin; OFX, ofloxacin; LVX, levofloxacin; MXF, moxifloxacin.

TABLE 12

MICs of quinolones against the chromosome-mediated resistance mechanisms, GyrA/ParC mutations and AcrAB-TolC overexpression (ΔramR) and/or the plasmid-mediated resistance mechanisms, QnrB, QnrS or AAC(6')-Ib-cr, in *K. pneumoniae* NVT1001

| Supplemental plasmid and antibiotic[a] | WT[c] | S83I | S83I/S80I | S83I/D87N/S80I | ΔramR | ΔramR/S83I | ΔramR/S83I/S80I | ΔramR/S83I/D87N/S80I |
|---|---|---|---|---|---|---|---|---|
| No | | | | | | | | |
| Nalidixic acid | 4 | >256 | >256 | >256 | 32 | >256 | >256 | >256 |
| Ciprofloxacin | 0.06 | 0.5 | 4 | 32 | 0.5 | 4 | >32 | >32 |
| Norfloxacin | 0.25 | 2 | 16 | 64 | 2 | 8 | 128 | >256 |
| Ofloxacin | 0.25 | 2 | 4 | 32 | 2 | >32 | >32 | >32 |
| Levofloxacin | 0.06 | 0.5 | 2 | 8 | 1 | 16 | >32 | >32 |
| Moxifloxacin | 0.125 | 1 | 8 | >32 | 1 | 8 | >32 | >32 |
| QnrB | | | | | | | | |
| Nalidixic acid | 32 | >256 | >256 | >256 | 256 | >256 | >256 | >256 |
| Ciprofloxacin | 0.5 | 2 | >32 | >32 | 4 | >32 | >32 | >32 |
| Norfloxacin | 2 | 8 | >256 | >256 | 16 | 64 | >256 | >256 |
| Ofloxacin | 4 | 8 | >32 | >32 | 32 | >32 | >32 | >32 |
| Levofloxacin | 1 | 2 | 16 | >32 | 8 | >32 | >32 | >32 |
| Moxifloxacin | 2 | 8 | >32 | >32 | >32 | >32 | >32 | >32 |
| QnrS | | | | | | | | |
| Nalidixic acid | 16 | >256 | >256 | >256 | 64 | >256 | >256 | >256 |
| Ciprofloxacin | 1 | 2 | >32 | >32 | 4 | 32 | >32 | >32 |
| Norfloxacin | 2 | 8 | 64 | 128 | 32 | 64 | >256 | >256 |
| Ofloxacin | 4 | 8 | >32 | >32 | 16 | >32 | >32 | >32 |
| Levofloxacin | 1 | 4 | 32 | >32 | 8 | >32 | >32 | >32 |
| Moxifloxacin | 1 | 8 | >32 | >32 | >32 | >32 | >32 | >32 |

TABLE 12-continued

MICs of quinolones against the chromosome-mediated resistance mechanisms, GyrA/ParC mutations and AcrAB-
TolC overexpression (ΔramR) and/or the plasmid-mediated resistance mechanisms, QnrB, QnrS or AAC(6')-Ib-cr, in
K. pneumoniae NVT1001

| Supplemental plasmid and antibiotic[a] | MIC (mg/L)[b] | | | | | | | |
|---|---|---|---|---|---|---|---|---|
| | WT[c] | S83I | S83I/S80I | S83I/D8 7N/S80I | ΔramR | ΔramR/ S83I | ΔramR/ S83I/S80I | ΔramR/S8 3I/D87N/ S80I |
| AAC(6')-Ib-cr | | | | | | | | |
| Nalidixic acid | 4 | >256 | >256 | >256 | 64 | >256 | >256 | >256 |
| Ciprofloxacin | 0.125 | 2 | 16 | >32 | 0.5 | 16 | >32 | >32 |
| Norfloxacin | 1 | 8 | 128 | >256 | 8 | 128 | >256 | >256 |
| Ofloxacin | 0.25 | 4 | 8 | 32 | 2 | >32 | >32 | >32 |
| Levofloxacin | 0.06 | 0.5 | 2 | 8 | 1 | 8 | >32 | >32 |
| Moxifloxacin | 0.125 | 1 | 8 | >32 | 1 | 16 | >32 | >32 |

[a]No, no supplemental plasmid. The Qnr protein or the aminoglycoside modifying enzyme on the low-copy-number plasmid pACYC177 is shown, and the plasmid was transferred into K. pneumoniae NVT1001 and its mutants.
[b]Boldface numbers indicate a significant (≥4-fold) difference in the MICs of the NVT1001 strain and its derived strains, while no significant (≥4-fold) differences in the MICs of the NVT1001 with or without plasmid pACYC177 alone (data not shown).
[c]WT, NVT1001; S83I, S83I mutant; S83I/S80I, S83I/S80I mutant; S83I/D87N/S80I, S83I/D87N/S80I mutant; ΔramR, ΔramR mutant; ΔramR/S83I, ΔramR/S83I mutant; ΔramR/S83I/S80I, ΔramR/S83I/S80I mutant; ΔramR/S83I/D87N/S80I, ΔramR/S83I/D87N/S80I mutant.

2.1.4 Aminoglycosides

The MICs of aminoglycosides for each resistance mechanism are shown in Table 13. Several different resistance profiles were found among the strains with different aminoglycoside-modifying enzymes, though all were susceptible to amikacin (Table 13). The production of 16S rRNA methylase, ArmA and RmtB was not associated with observable effects on the MIC of spectinomycin or streptomycin, whereas both conferred strong resistance to all other aminoglycosides tested (Table 13).

TABLE 13

MICs of aminoglycosides against the plasmid-mediated
resistance mechanism, aminoglycoside-modifying
enzyme or 16S rRNA methylase, in K. pneumoniae NVT1001

| Supplemental plasmid[a] | MIC (mg/L)b | | | | | | |
|---|---|---|---|---|---|---|---|
| | AMK[c] | GEN | KAN | NET | SPT | STR | TOB |
| No | 2 | 0.5 | 2 | 0.5 | 16 | 2 | 0.5 |
| AAC(3)-IId | 2 | 32 | 4 | 4 | 16 | 2 | 4 |
| AAC(3)-IVa | 2 | 32 | 8 | 64 | 16 | 2 | >256 |
| AAC(6')-Ib-cr | 8 | 0.25 | 32 | 8 | 16 | 2 | 8 |
| ANT(2'')-Ia | 2 | 64 | >256 | 1 | 16 | 2 | 64 |
| ANT(3'')-Ia | 2 | 0.25 | 2 | 0.5 | >1024 | 16 | 0.5 |
| APH(3')-Ia | 2 | 0.5 | >256 | 0.5 | 16 | 2 | 1 |
| APH(3')-IIa | 2 | 0.5 | >256 | 0.5 | 16 | 2 | 0.5 |
| StrA-StrB | 2 | 0.25 | 2 | 0.5 | 16 | 1024 | 0.5 |
| ArmA | >256 | >256 | >256 | >256 | 16 | 2 | >256 |
| RmtB | >256 | >256 | >256 | >256 | 16 | 2 | >256 |

[a]No, no supplemental plasmid. The aminoglycoside modifying enzyme or 16S rRNA methylases on the low-copy-number plasmid pACYC184 is shown, and the plasmid was transferred into K. pneumoniae NVT1001.
[b]Boldface numbers indicate a significant (≥4-fold) difference in the MICs of the NVT1001 strain and its derived strains, while no significant (≥4-fold) differences in the MICs of the NVT1001 with or without plasmid pACYC184 alone (data not shown).
[c]AMK, amikacin; GEN, gentamicin; KAN, kanamycin; NET, netilmicin; SPT, spectinomycin; STR, streptomycin; TOB, tobramycin.

2.1.5 Tetracyclines

The MICs of tetracyclines for various resistance mechanisms are shown in Table 14. With or without AcrAB-TolC overexpression (ΔramR), the production of Tet(B), Tet(C), Tet(D), or Tet(M) showed no observable effects on the MIC of tigecycline (Table 8). AcrAB-TolC overexpression (ΔramR) and Tet(A) production both conferred an 8-fold increase in the MIC of tigecycline, and a 32-fold increase was found when the two mechanisms were combined (Table 14).

TABLE 14

MICs of tetracyclines against the chromosome-mediated
resistance mechanism, AcrAB-
TolC overexpression (ΔramR), and/or the
plasmid-mediated resistance mechanism, the tet
resistance gene, in K. pneumoniae NVT1001

| Strain and antibiotic | MIC (mg/L)[a] | | | | | |
|---|---|---|---|---|---|---|
| | No[b] | Tet(A) | Tet(B) | Tet(C) | Tet(D) | Tet(M) |
| NVT1001 | | | | | | |
| Tetracycline | 4 | >256 | >256 | 16 | >256 | 16 |
| Doxycycline | 4 | >256 | >256 | 16 | 128 | 32 |
| Minocycline | 4 | 32 | 32 | 4 | 128 | 32 |
| Tigecycline | 1 | 8 | 1 | 1 | 1 | 1 |
| ΔramR | | | | | | |
| Tetracycline | 32 | >256 | >256 | 256 | >256 | 128 |
| Doxycycline | 64 | >256 | >256 | 128 | 256 | 128 |
| Minocycline | 64 | >256 | >256 | 64 | >256 | >256 |
| Tigecycline | 8 | 32 | 8 | 8 | 8 | 8 |

[a]Boldface numbers indicate a significant (≥4-fold) difference in the MICs of the NVT1001 strain and its derived strains, while no significant (≥4-fold) differences in the MICs of the NVT1001 with or without plasmid pACYC177 alone (data not shown).
[b]No, no supplemental plasmid. The tet resistance gene on the low-copy-number plasmid pACYC177 is shown, and the plasmid was transferred into K. pneumoniae NVT1001.

2.1.6 Folate Pathway Inhibitors

The MICs of folate pathway inhibitors against associated resistance mechanisms are shown in Table15. Strains with single resistance mechanisms were all susceptible (≤2/38 mg/L) to trimethoprim/sulfamethoxazole, and strains with certain combinations of mechanisms became resistant to trimethoprim/sulfamethoxazole (Table 15). Strains with porin loss and/or Sul production all showed no significant (≥4-fold) effects on the MIC of trimethoprim, whereas most of the other strains with combined mechanisms were associated with significant (≥4-fold) increases in the MICs of all folate pathway inhibitors tested (Table 15).

TABLE 15

MICs of folate pathway inhibitors against the chromosome-mediated resistance mechanism, OmpK35/36 loss and AcrAB-TolC overexpression (ΔramR), and/or the plasmid-mediated resistance mechanism, drug-resistant target enzyme, in *K. pneumoniae* NVT1001

| Supplemental plasmid and antibiotic[a] | MIC (mg/L)[b] | | | | | | | |
|---|---|---|---|---|---|---|---|---|
| | WT[c] | Δ35 | Δ36 | Δ35/36 | ΔramR | ΔramR Δ35 | ΔramR Δ36 | ΔramR Δ35/36 |
| No | | | | | | | | |
| Trimethoprim | 2 | 2 | 2 | 2 | 8 | 8 | 16 | >32 |
| Sulfamethoxazole | 256 | 256 | >1024 | >1024 | >1024 | >1024 | >1024 | >1024 |
| SXT | 0.25 | 0.25 | 0.5 | 0.5 | 0.5 | 0.5 | 1 | 8 |
| Sul1 | | | | | | | | |
| Trimethoprim | 2 | 2 | 2 | 4 | 16 | 32 | >32 | >32 |
| Sulfamethoxazole | >1024 | >1024 | >1024 | >1024 | >1024 | >1024 | >1024 | >1024 |
| SXT | 0.25 | 2 | 2 | 4 | 16 | 16 | >32 | >32 |
| Sul2 | | | | | | | | |
| Trimethoprim | 2 | 4 | 4 | 4 | 16 | 32 | 32 | >32 |
| Sulfamethoxazole | >1024 | >1024 | >1024 | >1024 | >1024 | >1024 | >1024 | >1024 |
| SXT | 1 | 2 | 2 | 2 | 8 | 8 | 16 | >32 |
| DfrA1 | | | | | | | | |
| Trimethoprim | >32 | >32 | >32 | >32 | >32 | >32 | >32 | >32 |
| Sulfamethoxazole | 256 | >1024 | >1024 | >1024 | >1024 | >1024 | >1024 | >1024 |
| SXT | 2 | 8 | >32 | >32 | >32 | >32 | >32 | >32 |
| DfrA16 | | | | | | | | |
| Trimethoprim | >32 | >32 | >32 | >32 | >32 | >32 | >32 | >32 |
| Sulfamethoxazole | 256 | >1024 | >1024 | >1024 | >1024 | >1024 | >1024 | >1024 |
| SXT | 1 | 4 | 8 | 16 | 4 | 4 | >32 | >32 |

[a]No, no supplemental plasmid. The drug-resistant target enzyme on the low-copy-number plasmid pACYC177 is shown, and the plasmid was transferred into *K. pneumoniae* NVT1001. SXT, trimethoprim/sulfamethoxazole (only the trimethoprim portion of the 1/19 drug ratio is displayed).
[b]Boldface numbers indicate a significant (≥4-fold) difference in the MICs of the NVT1001 strain and its derived strains, while no significant (≥4-fold) differences in the MICs of the NVT1001 with or without plasmid pACYC177 alone (data not shown).
[c]WT, NVT1001; Δ35, ΔompK35 mutant; Δ36, ΔompK36 mutant; Δ35/36, ΔompK35/36 mutant; ΔramR, ΔramR mutant; ΔramRΔ35, ΔramRΔompK35 mutant; ΔramRΔ6, ΔramRΔompK36 mutant; ΔramRΔ35/36, ΔramRΔompK35/36 mutant.

2.1.7 In Vivo Investigation

Figure 1B:
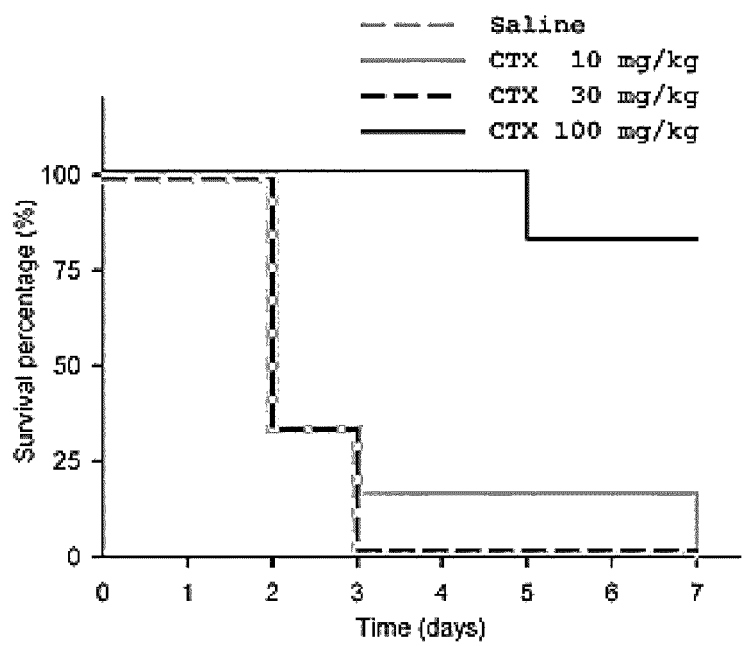

To further demonstrate that this system can also be used to test the efficacy of antibiotics in vivo, a mouse infection model was used. The 50% effective doses (ED50 values) of ceftazidime and cefotaxime were specifically determined using *K. pneumoniae* NVT1001 harbouring the pACYC177 plasmid with $bla_{OXA-48}$ (FIG. 1). The in vivo efficacy of ceftazidime was higher than that of cefotaxime, which had an estimated ED50 of 30 mg/kg, whereas no mice survived treatment with 30 mg/kg cefotaxime (FIG. 1). The higher efficacy of ceftazidime was also observed in the in vitro MIC assays, in which the MICs of ceftazidime and cefotaxime were 0.5 mg/L and 2 mg/L, respectively, using the broth microdilution test.

2.2 *A. baumannii* KW1

2.2.1 Efflux Pump Overexpression

The single mutation in the regulator genes of AdeABC efflux pump could significantly (≥4-fold) increase the MICs of ceftazidime, gentamicin, tetracycline and/or tigecycline, including D20N, A91V or P116L mutation in AdeR and G30D, A94V, R152K or T153M mutation in AdeS (Table 16). These mutations could also confer a 2 or 3-fold increase in the MIC of ciprofloxacin (Table 16).

2.2.2 Quinolones Target Site Mutation

The single mutation S83L in GyrA could significantly (4-fold) increase the MICs of all quinolones tested (Table 17). With the further mutation in ParC, including G78C, S80L,

TABLE 16

MICs of antibiotics against the chromosome-mediated resistance mechanism, AdeABC overexpression via AdeR or AdeS mutation, in *A. baumannii* KW1

| Strain | MIC (μg/ml)[a] | | | | |
|---|---|---|---|---|---|
| | CAZ[b] | CIP | GM | TC | TGC |
| KW1 | 4 | 0.25 | 0.75 | 3 | 0.25 |
| D20N mutant | 12 | 0.75 | 3 | 8 | 2 |
| A91V mutant | 16 | 0.75 | 4 | 12 | 3 |
| P116L mutant | 8 | 0.5 | 3 | 6 | 1.5 |
| G30D mutant | 8 | 0.75 | 4 | 8 | 3 |
| A94V mutant | 8 | 0.75 | 4 | 6 | 2 |
| R152K mutant | 8 | 0.75 | 4 | 6 | 2 |
| T153M mutant | 8 | 0.75 | 4 | 8 | 3 |

[a]Boldface numbers indicate a significant (≥4-fold) difference in the MICs of the KW1 strain and its mutants.
[b]CAZ, ceftazidime; CIP, ciprofloxacin; GM, gentamicin; TC, tetracycline; TGC, tigecycline.

S80W, S80Y or E84K mutation, could increase these MICs to high-level resistance (Table 17), whereas the single mutation of all these ParC mutations showed no significant (≥4-fold) effects on the MICs of any of the quinolones tested (Table 17).

TABLE 17

MICs of quinolones against the chromosome-mediated resistance mechanisms, GyrA and/or ParC mutations, in *A. baumannii* KW1

| Strain | MIC (µg/ml)[a] | | | | | |
|---|---|---|---|---|---|---|
| | NAL[b] | CIP | NOR | OFX | LVX | MXF |
| KW1 | 12 | 0.25 | 4 | 0.38 | 0.19 | 0.19 |
| S83L mutant | >256 | 2 | 24 | 6 | 1 | 0.75 |
| G78C mutant | 12 | 0.25 | 4 | 0.38 | 0.19 | 0.19 |
| S80L mutant | 12 | 0.25 | 4 | 0.5 | 0.19 | 0.25 |
| S80W mutant | 12 | 0.25 | 6 | 0.5 | 0.19 | 0.19 |
| S80Y mutant | 12 | 0.25 | 4 | 0.38 | 0.19 | 0.19 |
| E84K mutant | 12 | 0.25 | 4 | 0.38 | 0.19 | 0.19 |
| S83L/G78C mutant | >256 | 32 | >256 | 32 | 32 | 4 |
| S83L/S80L mutant | >256 | >32 | >256 | >32 | >32 | 6 |
| S83L/S80W mutant | >256 | >32 | >256 | >32 | >32 | 8 |
| S83L/S80Y mutant | >256 | >32 | >256 | >32 | >32 | 6 |
| S83L/E84K mutant | >256 | >32 | >256 | >32 | >32 | 6 |

[a]Boldface numbers indicate a significant (≥4-fold) difference in the MICs of the KW1 strain and its mutants.
[b]NAL, nalidixic acid; CIP, ciprofloxacin; NOR, norfloxacin; OFX, ofloxacin; LVX, levofloxacin; MXF, moxifloxacin.

2.2.3 Plasmid-Mediated Resistance Mechanism of β-Lactams

The MICs of β-lactams against associated resistance mechanisms are shown in Table 18. The production of CTX-M-15 or ADC-30 could significantly (≥4-fold) increase the MICs of all β-lactams tested. The production of each carbapenemase tested all showed no increase effects on the MIC of aztreonam, and no increase effects on the MIC of ceftazidime could also be found on the production of OXA-type carbapenemases tested in this study.

TABLE 18

MICs of β-lactams against the plasmid-mediated resistance mechanism, extended-spectrum β-lactamase, AmpC β-lactamase or carbapenemase, in *A. baumannii* KW1

| Supplemental plasmid[a] | MIC (µg/ml)[b] | | | | | |
|---|---|---|---|---|---|---|
| | ATM[c] | PP | CAZ | ETP | MP | DOR |
| No | 16 | 12 | 4 | 3 | 0.5 | 0.38 |
| pYMAb5 | 12 | 12 | 3 | 3 | 0.5 | 0.38 |
| CTX-M-15 | >256 | >256 | >256 | 12 | 2 | 1.5 |
| VEB-3 | >256 | 12 | >256 | 3 | 0.5 | 0.38 |
| ADC-30 | 64 | >256 | >256 | >32 | 3 | 4 |
| IMP-1 | 16 | 16 | 48 | >32 | 12 | 16 |
| NDM-1 | 12 | >256 | >256 | >32 | >32 | >32 |
| VIM-1 | 12 | >256 | >256 | >32 | >32 | >32 |
| OXA-23 | 16 | >256 | 3 | >32 | >32 | >32 |
| OXA-58 | 16 | 128 | 3 | >32 | 6 | 6 |
| OXA-66 | 12 | 64 | 3 | >32 | 8 | 8 |
| OXA-72 | 16 | >256 | 3 | >32 | >32 | >32 |

[a]No, no supplemental plasmid. The extended-spectrum β-lactamase, AmpC β-lactamase or carbapenemase on the shuttle vector pYMAb5 is shown, and the plasmid was transferred into *A. baumannii* KW1.
[b]Boldface numbers indicate a significant (≥4-fold) difference in the MICs of the KW1 strain and its derived strains.
[c]ATM, aztreonam; PP, piperacillin; PTc, piperacillin-tazobactam, tazobactam with a fixed concentration of 4 µg/ml; CAZ, ceftazidime; ETP, ertapenem; IP, imipenem; MP, meropenem; DOR, doripenem.

2.2.4 Plasmid-Mediated Resistance Mechanism of Aminoglycosides

The MICs of aminoglycosides for each resistance mechanism are shown in Table 19. Different resistance effects could be found on the production of these aminoglycoside-modifying enzymes, whereas all showed no increase effects on the MICs of amikacin, netilmicin and streptomycin. The production of 16S rRNA methylase, ArmA, was not associated with increase effects on the MICs of spectinomycin and streptomycin, whereas conferred strong resistance to all other aminoglycosides tested.

TABLE 19

MICs of aminoglycosides against the plasmid-mediated resistance mechanism, aminoglycoside-modifying enzyme or 16S rRNA methylase, in *A. baumannii* KW1

| Supplemental plasmid[a] | MIC (µg/ml)[b] | | | | | | |
|---|---|---|---|---|---|---|---|
| | AMK[c] | GEN | KAN | NET | SPT | STR | TOB |
| No | 2 | 0.5 | 2 | 1.5 | 24 | 12 | 0.5 |
| pYMAb5Tc | 2 | 0.5 | 2 | 1.5 | 24 | 12 | 0.5 |
| AAC(3)-IIa | 2 | 3 | 2 | 1.5 | 24 | 8 | 0.5 |
| ANT(2")-Ia | 2 | 3 | 4 | 1.5 | 24 | 8 | 2 |
| ANT(3")-Ia | 2 | 0.5 | 2 | 1.5 | 192 | 8 | 0.5 |
| APH(3')-Ia | 2 | 0.5 | 16 | 1.5 | 24 | 12 | 0.5 |
| APH(3')-VIa | 2 | 0.5 | 16 | 1.5 | 24 | 12 | 0.5 |
| ArmA | >256 | >256 | >256 | >256 | 24 | 8 | >256 |

[a]No, no supplemental plasmid. The aminoglycoside modifying enzyme or 16S rRNA methylase on the shuttle vector pYMAb5Tc is shown, and the plasmid was transferred into *A. baumannii* KW1.
[b]Boldface numbers indicate a significant (≥4-fold) difference in the MICs of the KW1 strain and its derived strains.
[c]AMK, amikacin; GEN, gentamicin; KAN, kanamycin; NET, netilmicin; SPT, spectinomycin; STR, streptomycin; TOB, tobramycin.

2.2.5 Plasmid-Mediated Resistance Mechanism of Tetracyclines

The MICs of tetracyclines for its resistance mechanisms are shown in Table 20. The production of Tet(A), Tet(B) or Tet(C) could significantly (4-fold) increase the MICs of tetracycline, doxycycline and minocycline. In the MICs of tigecycline, the production of Tet(B) or Tet(M) showed no observable effects, whereas the production of Tet(A) could confer a 2 to 3-fold increase.

TABLE 20

MICs of tetracyclines against the plasmid-mediated resistance mechanism, tet resistance gene, in *A. baumannii* KW1

| Supplemental plasmid[a] | MIC (µg/ml)[b] | | | |
|---|---|---|---|---|
| | TC[c] | DC | MC | TGC |
| No | 3 | 0.75 | 0.38 | 0.38 |
| pYMAb5 | 3 | 0.75 | 0.25 | 0.38 |
| Tet(A) | 128 | 12 | 1.5 | 1 |
| Tet(B) | >256 | 32 | 1.5 | 0.38 |
| Tet(M) | 48 | 192 | 2 | 0.38 |

[a]No, no supplemental plasmid. The tet resistance genes on the shuttle vector pYMAb5 is shown, and the plasmid was transferred into *A. baumannii* KW1.
[b]Boldface numbers indicate a significant (≥4-fold) difference in the MICs of the KW1 strain and its derived strains.
[c]TC, tetracycline; DC, doxycycline; MC, Minocycline; TGC, tigecycline.

3. Discussion

In this study, 193 genetically engineered strains with different resistance mechanisms were constructed from *K. pneumoniae* NVT1001, a fully susceptible clinical isolate, including 29 strains with chromosome-mediated resistance, 33 strains with plasmid-mediated resistance and 131 strains with a combination of the two resistance mechanisms. In addition, 37 genetically engineered strains with different resistance mechanisms were constructed from *A. baumannii* KW1, a fully susceptible clinical isolate, including 18 strains with chromosome-mediated resistance and 19 strains with plasmid-mediated resistance. Because the resistance mechanisms of these strains were constructed, all are known to be resistant to specific antibiotics. In addition, the plasmid-mediated resistance mechanisms were constructed using non-conjugative plasmids without transposons, so these mechanisms are not easy to spread. These features suggest that using these strains is safer than using drug-resistant clinical isolates.

Also in contrast to clinical drug-resistant isolates, these genetically engineered strains have clear and simple antibiotic resistance mechanisms. In in vitro MIC assays, the resistance profiles of these strains were confirmed by testing the MICs against several well-known antibiotics. Investigators can estimate the effectiveness of their antibiotics by comparing their MIC results to those of well-known antibiotics. The MIC assay is usually the starting point for assessing antibiotics, and our results suggest that these strains were ready for testing antibiotic activities in vitro.

In vivo mouse infection models are commonly used to demonstrate the efficacy of antibiotics in protecting against lethal infection.[28-30] Using a clinical *K. pneumoniae* isolate producing the carbapenemase OXA-48, a previous study found that the MIC of ceftazidime was 4-fold lower than that of cefotaxime and that the ED50 of ceftazidime was lower than that of cefotaxime.[28] A similar result was obtained in the present study using *K. pneumoniae* NVT1001 harbouring the pACYC177 plasmid with $bla_{OXA-48}$. In contrast to many other clinical isolates, this genetically engineered strain can effectively infect BALB/c mice without weakening their immune system, and its 100% lethal dose (LD100) is $4 \times 10^3$ cfu in the mouse infection model, similar to its parental strain NVT1001 (data not shown). Obtained without changing the immune system of mice, the in vivo results should be closer to the true antibiotic efficacy during clinical use. The results thus suggest that these genetically engineered strains are adequate for testing antibiotic activities in vivo.

For the development of antibiotics in the face of multidrug resistance, in vitro selection and earlier evaluation are important steps before in vivo studies and further clinical evaluation. In contrast to the use of clinical isolates, the use of the platform technology described here to evaluate antibiotics may elucidate the exact reason for and the level of resistance both in vitro and in vivo. This information may in turn help in estimation of the efficacy of and potential resistance to antibiotics. The modification of antibiotics' chemical structure and discontinuities in development can lower the costs associated with the development process. Furthermore, the global prevalence and distribution of antibiotic resistance genes are already available from various studies and monitoring groups.[31-36] In combination with these data, the data obtained from this platform technology may also help in estimation of the rates of resistance to newly developed drugs across regions. Additionally, antibiotics should be used more carefully in regions where specific resistance mechanisms are epidemic.

The set of resistant strains included in this platform technology can be expanded. Specifically, through genetic construction, other resistance mechanisms or different combinations of mechanisms can also be constructed in the same parental strain, including newly identified mechanisms. Given that the genetic background of several important bacterial pathogens with high resistance rates is quite different from that of *K. pneumoniae*, specific resistance genes can be found in these pathogens.[37,38] For example, the overexpression of the AdeABC efflux pump can confer antibiotic resistance in *A. baumannii*, whereas this efflux pump does not exist in *K. pneumoniae*.[37] To completely evaluate the activities of antibiotics, these specific resistance mechanisms should also be constructed in their original pathogens; in fact, several of them have been successfully constructed by our group (data not shown).

In summary, various chromosomal and plasmid resistance mechanisms were constructed in this study, and especially mechanisms conferring resistance to β-lactams, quinolones, aminoglycosides, tetracyclines or folate pathway inhibitors, in fully susceptible bacterial strains. Our results demonstrate that this platform technology can be used to efficiently and effectively evaluate antibiotics targeting specific resistance mechanisms both in vitro and in vivo. The system can also be used to screen new antibiotics against multidrug-resistant bacteria.

REFERENCES

1 O'Neill J, chair. Tackling drug-resistant infections globally: final report and recommendations. *Review on Antimicrobial Resistance*, London, United Kingdom 2016.

2 Boucher H W, Talbot G H, Benjamin D K et al. 10×'20 Progress—development of new drugs active against gram-negative bacilli: an update from the Infectious Diseases Society of America. *Clin Infect Dis* 2013; 56: 1685-94.

3 WHO. Global priority list of antibiotic-resistant bacteria to guide research, discovery, and development of new antibiotics. *World Health Organization* 2017. http://www.who.int/medicines/publications/global-priority-list-antibiotic-resistant-bacteriden/.

4 WHO. Antimicrobial resistance: global report on surveillance. *World Health Organization* 2014. http://www.who.int/drugresistance/documents/surveillancereport/en/.

5 Iredell J, Brown J, Tagg K. Antibiotic resistance in Enterobacteriaceae: mechanisms and clinical implications. *BMJ* 2016; 352.

6 Mendes R E, Castanheira M, Gasink L et al. β-lactamase characterization of gram-negative pathogens recovered from patients enrolled in the phase 2 trials for ceftazidime-avibactam: clinical efficacies analyzed against subsets of molecularly characterized isolates. *Antimicrob Agents Chemother* 2015; 60: 1328-35.

7 Tsai Y K, Fung C P, Lin J C et al. *Klebsiella pneumoniae* outer membrane porins OmpK35 and OmpK36 play roles in both antimicrobial resistance and virulence. *Antimicrob Agents Chemother* 2011; 55: 1485-93.

8 Wang X, Chen H, Zhang Y et al. Genetic characterisation of clinical *Klebsiella pneumoniae* isolates with reduced susceptibility to tigecycline: Role of the global regulator RamA and its local repressor RamR. *Int J Antimicrob Agents* 2015; 45: 635-40.

9 Bailey A M, Ivens A, Kingsley R et al. RamA, a member of the AraC/XylS family, influences both virulence and efflux in *Salmonella enterica* serovar Typhimurium. *J Bacteriol* 2010; 192: 1607-16.

10 Bialek-Davenet S, Leflon-Guibout V, Tran Minh O et al. Complete deletion of the ramR gene in an in vitro-selected mutant of *Klebsiella pneumoniae* overexpressing the AcrAB efflux pump. *Antimicrob Agents Chemother* 2013; 57: 672-3.

11 Blanco P, Hernando-Amado S, Reales-Calderon J A et al. Bacterial multidrug efflux pumps: much more than antibiotic resistance determinants. *Microorganisms* 2016; 4.

12 Stoesser N, Batty E M, Eyre D W et al. Predicting antimicrobial susceptibilities for *Escherichia coli* and *Klebsiella pneumoniae* isolates using whole genomic sequence data. *J Antimicrob Chemother* 2013; 68: 2234-44.

13 Ruiz E, Saenz Y, Zarazaga M et al. qnr, aac(6')-Ib-cr and qepA genes in *Escherichia coli* and *Klebsiella* spp.: genetic environments and plasmid and chromosomal location. *J Antimicrob Chemother* 2012; 67: 886-97.

14 Rodriguez-Martinez J M, Diaz de Alba P, Briales A et al. Contribution of OqxAB efflux pumps to quinolone resistance in extended-spectrum-β-lactamase-producing *Klebsiella pneumoniae*. *J Antimicrob Chemother* 2013; 68: 68-73.

15 Fu Y, Guo L, Xu Y et al. Alteration of GyrA amino acid required for ciprofloxacin resistance in *Klebsiella pneumoniae* isolates in China. *Antimicrob Agents Chemother* 2008; 52: 2980-3.

16 Roberts M C, Schwarz S, Aarts H J. Commentary on "Acquired antibiotic resistance genes: an overview". *Front Microbiol* 2012; 3.

17 Yeh K M, Kurup A, Siu L K et al. Capsular serotype K1 or K2, rather than magA and rmpA, is a major virulence determinant for *Klebsiella pneumoniae* liver abscess in Singapore and Taiwan. *J Clin Microbiol* 2007; 45: 466-71.

18 Yeh K M, Lin J C, Yin F Y et al. Revisiting the importance of virulence determinant magA and its surrounding genes in *Klebsiella pneumoniae* causing pyogenic liver abscesses: exact role in serotype K1 capsule formation. *J Infect Dis* 2010; 201: 1259-67.

19 Tsai Y K, Liou C H, Lin J C et al. A suitable streptomycin-resistant mutant for constructing unmarked in-frame gene deletions using rpsL as a counter-selection marker. *PloS one* 2014; 9: e109258.

20 Reyrat J-M, Pelicic V, Gicquel B et al. Counterselectable markers: untapped tools for bacterial genetics and pathogenesis. *Infect Immun* 1998; 66: 4011-7.

21 Ho S N, Hunt H D, Horton R M et al. Site-directed mutagenesis by overlap extension using the polymerase chain reaction. *Gene* 1989; 77: 51-9.

22 Horton R M, Hunt H D, Ho S N et al. Engineering hybrid genes without the use of restriction enzymes: gene splicing by overlap extension. *Gene* 1989; 77: 61-8.

23 Skorupski K, Taylor R K. Positive selection vectors for allelic exchange. *Gene* 1996; 169: 47-52.

24 Ohtomo R, Saito M. A new selective medium for detection of *Klebsiella* from dairy environments. *Microbes Environ* 2003; 18: 138-44.

25 Clinical and Laboratory Standards Institute. *Performance Standards for Antimicrobial Susceptibility Testing: Twenty-seventh Informational Supplement M*100-S27. CLSI, Wayne, Pa., USA, 2017.

26 Clinical and Laboratory Standards Institute. *Performance Standards for Antimicrobial Susceptibility Testing: Twenty-fifth Informational Supplement M*100-S25. CLSI, Wayne, Pa., USA, 2015.

27 EUCAST. The European Committee on Antimicrobial Susceptibility Testing. Breakpoint tables for interpretation of MICs and zone diameters. Version 7.1, 2017.

28 Mimoz O, Grégoire N, Poirel L et al. Broad-spectrum β-lactam antibiotics for treating experimental peritonitis in mice due to *Klebsiella pneumoniae* producing the carbapenemase OXA-48. *Antimicrob Agents Chemother* 2012; 56: 2759-60.

29 Reyes N, Aggen J B, Kostrub C F. In vivo efficacy of the novel aminoglycoside ACHN-490 in murine infection models. *Antimicrob Agents Chemother* 2011; 55: 1728-33.

30 Knudsen J D, Fuursted K, Frimodt-Møller N et al. Comparison of the effect of cefepime with four cephalosporins against pneumococci with various susceptibilities to penicillin, in vitro and in the mouse peritonitis model. *J Antimicrob Chemother* 1997; 40: 679-86.

31 van Duin D, Doi Y. The global epidemiology of carbapenemase-producing Enterobacteriaceae. *Virulence* 2016: 1-10.

32 Tangden T, Giske C G. Global dissemination of extensively drug-resistant carbapenemase-producing Enterobacteriaceae: clinical perspectives on detection, treatment and infection control. *J Intern Med* 2015; 277: 501-12.

33 Wachino J, Arakawa Y. Exogenously acquired 16S rRNA methyltransferases found in aminoglycoside-resistant pathogenic Gram-negative bacteria: an update. *Drug Resist Updat* 2012; 15: 133-48.

34 Nordmann P, Naas T, Poirel L. Global spread of carbapenemase-producing Enterobacteriaceae. *Emerg Infect Dis* 2011; 17: 1791-8.

35 Gupta N, Limbago B M, Patel J B et al. Carbapenem-resistant Enterobacteriaceae: epidemiology and prevention. *Clin Infect Dis* 2011; 53: 60-7.

36 Hawkey P M, Jones A M. The changing epidemiology of resistance. *J Antimicrob Chemother* 2009; 64: i3-i10.

37 Santajit S, Indrawattana N. Mechanisms of antimicrobial resistance in ESKAPE pathogens. *Biomed Res Int* 2016; 2016: 2475067.

38 Rice L B. Federal funding for the study of antimicrobial resistance in nosocomial pathogens: no ESKAPE. *J Infect Dis* 2008; 197: 1079-81.

39. WHO. 2017. Global priority list of antibiotic-resistant bacteria to guide research, discovery, and development of new antibiotics. World Health Organization.

40. Lin C T, Wu C C, Chen Y S, Lai Y C, Chi C, Lin J C, Chen Y, Peng H L. 2011. Fur regulation of the capsular polysaccharide biosynthesis and iron-acquisition systems in *Klebsiella pneumoniae* CG43. Microbiology 157:419-429.

41. Yoon E J, Courvalin P, Grillot-Courvalin C. 2013. RND-type efflux pumps in multidrug-resistant clinical isolates of *Acinetobacter baumannii*: major role for AdeABC overexpression and AdeRS mutations. Antimicrob Agents Chemother 57:2989-95.

42. Hornsey M, Loman N, Wareham D W, Ellington M J, Pallen M J, Turton J F, Underwood A, Gaulton T, Thomas C P, Doumith M, Livermore D M, Woodford N. 2011. Whole-genome comparison of two *Acinetobacter baumannii* isolates from a single patient, where resistance developed during tigecycline therapy. J Antimicrob Chemother 66:1499-503.

43. Hornsey M, Ellington M J, Doumith M, Thomas C P, Gordon N C, Wareham D W, Quinn J, Lolans K, Livermore D M, Woodford N. 2010. AdeABC-mediated efflux and tigecycline MICs for epidemic clones of *Acinetobacter baumannii*. Journal of Antimicrobial Chemotherapy 65:1589-1593.

44. Coyne S, Guigon G, Courvalin P, Perichon B. 2010. Screening and quantification of the expression of antibiotic resistance genes in *Acinetobacter baumannii* with a microarray. Antimicrob Agents Chemother 54:333-40.

45. Higgins P G, Schneiders T, Hamprecht A, Seifert H. 2010. In vivo selection of a missense mutation in adeR and conversion of the novel bla$_{OXA-164}$ gene into bla$_{OXA-58}$ in carbapenem-resistant *Acinetobacter baumannii* isolates from a hospitalized patient. Antimicrobial Agents and Chemotherapy 54:5021-5027.

46. Marchand I, Damier-Piolle L, Courvalin P, Lambert T. 2004. Expression of the RND-type efflux pump AdeABC in *Acinetobacter baumannii* is regulated by the AdeRS two-component system. Antimicrobial Agents and Chemotherapy 48:3298-3304.

47. Ardebili A, Lari A R, Beheshti M, Lari E R. 2015. Association between mutations in gyrA and parC genes of *Acinetobacter baumannii* clinical isolates and ciprofloxacin resistance. Iran J Basic Med Sci 18:623-6.

48. Lopes B S, Amyes S G. 2013. Insertion sequence disruption of adeR and ciprofloxacin resistance caused by efflux pumps and gyrA and parC mutations in *Acinetobacter baumannii*. Int J Antimicrob Agents 41:117-21.
49. Liu Y H, Kuo S C, Lee Y T, Chang I C, Yang S P, Chen T L, Fung C P. 2012. Amino acid substitutions of quinolone resistance determining regions in GyrA and ParC associated with quinolone resistance in *Acinetobacter baumannii* and *Acinetobacter genomic* species 13TU. J Microbiol Immunol Infect 45:108-12.
50. Park S, Lee K M, Yoo Y S, Yoo J S, Yoo J I, Kim H S, Lee Y S, Chung G T. 2011. Alterations of gyrA, gyrB, and parC and activity of efflux pump in fluoroquinolone-resistant *Acinetobacter baumannii*. Osong Public Health and Research Perspectives 2:164-170.
51. Mak J K, Kim M J, Pham J, Tapsall J, White P A. 2009. Antibiotic resistance determinants in nosocomial strains of multidrug-resistant *Acinetobacter baumannii*. J Antimicrob Chemother 63:47-54.
52. Hamouda A, Amyes S G. 2004. Novel gyrA and parC point mutations in two strains of *Acinetobacter baumannii* resistant to ciprofloxacin. J Antimicrob Chemother 54:695-6.
53. Vila J, Ruiz J, Goni P, Jimenez de Anta T. 1997. Quinolone-resistance mutations in the topoisomerase IV parC gene of *Acinetobacter baumannii*. J Antimicrob Chemother 39:757-62.
54. Karah N, Haldorsen B, Hegstad K, Simonsen G S, Sundsfjord A, Samuelsen Ø. 2011. Species identification and molecular characterization of *Acinetobacter* spp. blood culture isolates from Norway. Journal of Antimicrobial Chemotherapy 66:738-744.
55. Roberts M C, Schwarz S, Aarts H J. 2012. Commentary on "Acquired antibiotic resistance genes: an overview". Frontiers in Microbiology 3.
56. Yeh K M, Lin J C, Yin F Y, Fung C P, Hung H C, Siu L K, Chang F Y. 2010. Revisiting the importance of virulence determinant magA and its surrounding genes in *Klebsiella pneumoniae* causing pyogenic liver abscesses: exact role in serotype K1 capsule formation. J Infect Dis 201:1259-67.
57. Tsai Y K, Liou C H, Lin J C, Ma L, Fung C P, Chang F Y, Siu L K. 2014. A suitable streptomycin-resistant mutant for constructing unmarked in-frame gene deletions using rpsL as a counter-selection marker. PLoS One 9:e109258.
58. Reyrat J-M, Pelicic V, Gicquel B, Rappuoli R. 1998. Counterselectable markers: untapped tools for bacterial genetics and pathogenesis. Infect Immun 66:4011-4017.

What is claimed is:

1. A method for screening for an antimicrobial agent, comprising
   (1) providing a wild-type (WT) susceptible bacterial strain;
   (2) providing a genetic engineering (GE) resistant bacterial strain generated from the WT susceptible bacterial strain via a genetic engineering manner to confer a drug resistance based on one or more drug resistant mechanisms selected from the group consisting of (i) decrease antibiotic permeability by loss of outer membrane proteins, (ii) pump out the antibiotics by overexpression of efflux pumps, (iii) eliminates or reduces binding of antibiotic by modification of antibiotic target or by acquirement of antibiotic-resistant target, (iv) inactivate antibiotic by enzymatic cleavage or modification;
   (3) culturing the WT susceptible bacterial strain in the presence of a test agent and measuring a minimum inhibitory concentration (MIC) value of the test agent against the WT susceptible bacterial strain;
   (4) culturing the GE resistant bacterial strain in the presence of the test agent and measuring a MIC value of the test agent against the GE resistant bacterial strain;
   (5) comparing the MIC value of the test agent against the WT susceptible bacterial strain as defined in Step (3) with the MIC value of the test agent against the GE resistant bacterial strain as defined in Step (4) to obtain a comparison result; and
   (6) determining whether the test agent is a potentially effective antimicrobial agent against the drug resistance based on the comparison result of Step (5), wherein an insignificant difference between the MIC value of the test agent against the GE resistant bacterial strain as defined in Step (4) and the MIC value of the test agent against the WT susceptible bacterial strain as defined in Step (3) indicates that the test agent is a potentially effective antimicrobial agent against the drug resistance.

2. The method of claim 1, wherein a ratio of the MIC value of the test agent against the GE resistant bacterial strain as defined in Step (4) to the MIC value of the test agent against the WT susceptible bacterial strain as defined in Step (3) being no more than 4 is indicative of insignificant difference in the comparison result of Step (5).

3. The method of claim 1, wherein the GE resistant bacterial strain includes one or more mutations or an antibiotic resistance gene selected from the group consisting of ΔompK35, ΔompK36, ΔramR, GyrA S83I, GyrA S83L, GyrA S83F, GyrA S83Y, GyrA D87N, GyrA S80I, CTX-M-14, CTX-M-15, SHV-12, CMY-2, DHA-1-AmpR, KPC-2, KPC-3, IMP-8, NDM-1, VIM-1, OXA-48, QnrB, QnrS, AAC(6')-Ib-cr, AAC(6')-Ib-cr, AAC(3)-IId, AAC(3)-IVa, ANT(2")-Ia, ANT(3")-Ia, APH(3')-Ia, APH(3')-IIa, StrA-StrB, ArmA, RmtB, Tet(A), Tet(B), Tet(C), Tet(D), Tet(M), Sul1, Sul2, DfrA1, DfrA16, AdeR D20N, AdeR A91V, AdeR P116L, AdeS G30D, AdeS A94V, AdeS R152K, AdeS T153M, ParC G78C, ParC S80L, ParC S80W, ParC 580Y, ParC E84K, VEB-3, ADC-30, IMP-1, OXA-23, OXA-58, OXA-66, OXA-72, AAC(3)-IIa, APH(3')-VIa, and any combinations thereof.

4. The method of claim 1, wherein the bacterial strain is of *K. pneumonia, Escherichia coli, Salmonella* spp., *Acinetobacter baumannii, Pseudomonas aeruginosa* or *Staphylococcus aureus*.

5. The method of claim 1, the bacterial strain is *K. pneumonia* NVT1001.

6. The method of claim 1, the bacterial strain is *A. baumannii* KW1.

* * * * *

```
                        SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: acrA-qF primer

<400> SEQUENCE: 1
atgtgacgat aaaccggctc                                              20

<210> SEQ ID NO 2
<211> LENGTH: 20
<212> TYPE: DNA
<213> ORGANISM: Artificial Sequence
<220> FEATURE:
<223> OTHER INFORMATION: acrA-qR primer

<400> SEQUENCE: 2
ctggcagttc ggtggttatt                                              20

<210> SEQ ID NO 3
<211> LENGTH: 21
<212> TYPE: DNA
<213> ORGANISM: Artificial Sequence
<220> FEATURE:
<223> OTHER INFORMATION: tolC-qF primer

<400> SEQUENCE: 3
aacgggcaga accaaatcgg c                                            21

<210> SEQ ID NO 4
<211> LENGTH: 22
<212> TYPE: DNA
<213> ORGANISM: Artificial Sequence
<220> FEATURE:
<223> OTHER INFORMATION: tolC-qR

<400> SEQUENCE: 4
```

```
cgttgatgct gctgatggag gc                                          22

<210> SEQ ID NO 5
<211> LENGTH: 24
<212> TYPE: DNA
<213> ORGANISM: Artificial Sequence
<220> FEATURE:
<223> OTHER INFORMATION: ramA-qF primer

<400> SEQUENCE: 5
tgattcgcaa cagactttta cccg                                        24

<210> SEQ ID NO 6
<211> LENGTH: 23
<212> TYPE: DNA
<213> ORGANISM: Artificial Sequence
<220> FEATURE:
<223> OTHER INFORMATION: ramA-qR primer

<400> SEQUENCE: 6
gcgactgtgg ttctctttgc ggt                                         23

<210> SEQ ID NO 7
<211> LENGTH: 20
<212> TYPE: DNA
<213> ORGANISM: Artificial Sequence
<220> FEATURE:
<223> OTHER INFORMATION: ramR-qF primer

<400> SEQUENCE: 7
aggatgagtt gctcaacgag                                             20

<210> SEQ ID NO 8
<211> LENGTH: 22
<212> TYPE: DNA
<213> ORGANISM: Artificial Sequence
<220> FEATURE:
<223> OTHER INFORMATION: ramR-qR primer

<400> SEQUENCE: 8
ccagtcgata tagctgttcc ag                                          22

<210> SEQ ID NO 9
<211> LENGTH: 20
<212> TYPE: DNA
<213> ORGANISM: Artificial Sequence
<220> FEATURE:
<223> OTHER INFORMATION: 23S-qF primer

<400> SEQUENCE: 9
ggtaggggag cgttctgtaa                                             20

<210> SEQ ID NO 10
<211> LENGTH: 20
<212> TYPE: DNA
<213> ORGANISM: Artificial Sequence
<220> FEATURE:
<223> OTHER INFORMATION: 23S-qR primer

<400> SEQUENCE: 10
tcagcattcg cacttctgat                                             20
```